United States Patent
Kumar et al.

(10) Patent No.: US 12,079,851 B2
(45) Date of Patent: *Sep. 3, 2024

(54) ONBOARDING PLATFORM FOR PERFORMING DYNAMIC MITIGATION ANALYSIS

(71) Applicant: Allstate Insurance Company, Northbrook, IL (US)

(72) Inventors: Surender Kumar, Palatine, IL (US); Philip Peter Ramirez, Arlington Heights, IL (US); Howard Hayes, Glencoe, IL (US); Matthew Olenak, Chicago, IL (US); Avani Patel, Chicago, IL (US); Araba Appiagyei-Dankah, Chicago, IL (US); John Rugel, Hawthorn Woods, IL (US)

(73) Assignee: ALLSTATE INSURANCE COMPANY, Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/667,628

(22) Filed: Oct. 29, 2019

(65) Prior Publication Data

US 2020/0211075 A1   Jul. 2, 2020

Related U.S. Application Data

(63) Continuation-in-part of application No. 16/238,050, filed on Jan. 2, 2019, now Pat. No. 11,574,357, and a
(Continued)

(51) Int. Cl.
*G06Q 30/0601* (2023.01)
*G06F 3/01* (2006.01)
(Continued)

(52) U.S. Cl.
CPC ......... *G06Q 30/0607* (2013.01); *G06F 3/015* (2013.01); *G06N 20/00* (2019.01);
(Continued)

(58) Field of Classification Search
CPC ........ G06N 20/00–20; G06F 3/00–167; G06Q 20/00–425; G06Q 30/00–08; G16H 20/00–90
See application file for complete search history.

(56) References Cited

U.S. PATENT DOCUMENTS 6,871,287 B1   3/2005   Ellingson
7,278,025 B2   10/2007   Saito et al.
(Continued)

FOREIGN PATENT DOCUMENTS

CN   107133438 A   *   9/2017

OTHER PUBLICATIONS

Clark, Lisa. Stakeholders: Bullet List of Legal Considerations. Mondaq Business Briefing. May 29, 2012 (Year: 2012).*
(Continued)

*Primary Examiner* — Linh Giang Le
(74) *Attorney, Agent, or Firm* — Polsinelli PC

(57) ABSTRACT

Aspects of the disclosure relate to computing platforms that utilize improved mitigation analysis and policy management techniques to improve onboarding security. A computing platform may determine that a predetermined period of time has elapsed since finalizing an onboarding process. The computing platform may receive spot-check verification inputs indicative of a user identity and may direct a mitigation analysis and output generation platform to analyze the spot-check verification inputs. The computing platform may receive an indication of a correlation between the spot-check verification inputs and expected spot-check verification inputs. In response to determining that the correla-
(Continued)

tion exceeds a predetermined threshold, the computing platform may determine that an additional verification test should be conducted, and may direct a mobile or other computing device to display an interface that prompts for additional onboarding verification inputs.

20 Claims, 23 Drawing Sheets

Related U.S. Application Data continuation-in-part of application No. 16/238,021, filed on Jan. 2, 2019, now Pat. No. 11,481,732.

(51) Int. Cl.
*G06N 20/00* (2019.01)
*G06Q 20/40* (2012.01)
*G16H 20/10* (2018.01)
*G16H 50/30* (2018.01)

(52) U.S. Cl.
CPC ....... *G06Q 20/40145* (2013.01); *G16H 20/10* (2018.01); *G16H 50/30* (2018.01)

(56) References Cited

U.S. PATENT DOCUMENTS

| | | | |
|---|---|---|---|
| 7,548,886 B2 | 6/2009 | Kirkland et al. | |
| 7,686,214 B1 | 3/2010 | Shao et al. | |
| 8,103,543 B1 | 1/2012 | Zwicky | |
| 8,185,463 B1 | 5/2012 | Ball | |
| 8,185,747 B2 | 5/2012 | Wood et al. | |
| 8,401,878 B2 | 3/2013 | Stender et al. | |
| 8,984,606 B2 | 3/2015 | Kamat | |
| 9,119,539 B1 | 9/2015 | Dotan et al. | |
| 9,147,117 B1 | 9/2015 | Madhu et al. | |
| 9,391,986 B2 | 7/2016 | Schultz et al. | |
| 9,697,660 B1 | 7/2017 | Sokolov et al. | |
| 9,794,260 B2 | 10/2017 | Loughlin-McHugh et al. | |
| 10,432,892 B1 | 10/2019 | Tamayo et al. | |
| 10,581,612 B2 | 3/2020 | Landrock et al. | |
| 10,812,479 B2 | 10/2020 | Apturkar et al. | |
| 2003/0055767 A1 | 3/2003 | Tamura et al. | |
| 2003/0112120 A1 | 6/2003 | K. | |
| 2005/0283388 A1 | 12/2005 | Eberwine et al. | |
| 2006/0136595 A1 | 6/2006 | Satyavolu | |
| 2008/0016099 A1 | 1/2008 | Ikeda | |
| 2009/0182583 A1 | 7/2009 | Harkensee et al. | |
| 2009/0182585 A1 | 7/2009 | Harkensee et al. | |
| 2010/0131304 A1 | 5/2010 | Collopy et al. | |
| 2013/0055367 A1* | 2/2013 | Kshirsagar | G06F 21/32 726/6 |
| 2013/0090950 A1 | 4/2013 | Rao | |
| 2013/0204645 A1* | 8/2013 | Lehman | G06Q 40/08 705/4 |
| 2013/0226623 A1 | 8/2013 | Diana et al. | |
| 2013/0332286 A1 | 12/2013 | Medelius et al. | |
| 2014/0018686 A1 | 1/2014 | Medelius et al. | |
| 2014/0041017 A1 | 2/2014 | Wentworth et al. | |
| 2015/0178581 A1 | 6/2015 | Aoki | |
| 2016/0155126 A1 | 6/2016 | D'Uva | |
| 2017/0011195 A1 | 1/2017 | Arshad et al. | |
| 2018/0315127 A1 | 11/2018 | Chappell et al. | |
| 2019/0079782 A1 | 3/2019 | Goldberg et al. | |
| 2019/0141039 A1 | 5/2019 | Stoops et al. | |
| 2019/0312879 A1 | 10/2019 | Agrawal et al. | |
| 2019/0313367 A1 | 10/2019 | Ryu et al. | |
| 2020/0089848 A1 | 3/2020 | Abdelaziz et al. | |
| 2020/0186522 A1 | 6/2020 | Apturkar et al. | |
| 2021/0056641 A1 | 2/2021 | Fitzgerald et al. | |

OTHER PUBLICATIONS

Jun. 21, 2021—(US) Final Office Action—U.S. Appl. No. 16/238,021.

Sep. 28, 2022—(US) Notice of Allowance—U.S. Appl. No. 16/238,050, 23 Pages.

Apr. 19, 2022—(US) Non-Final Office Action—U.S. Appl. No. 16/238,050, 18 Pages.

Dec. 14, 2023—(US) Non-Final Office Action—U.S. Appl. No. 18/106,523, 21 Pages.

Sep. 14, 2023—(US) Non-Final Office Action—U.S. Appl. No. 17/971,946, 14 Pages.

Mar. 25, 2024—(US) Final Office Action—U.S. Appl. No. 17/971,946, 20 Pages.

Apr. 2, 2024—(US) Final Office Action—U.S. Appl. No. 18/106,523, 44 Pages.

"Shufti Pro" https://shuftipro.com/technology/ website visited Sep. 5, 2018 pp. 1-9.

"When Identity Matters" https://www.jumio.com/ website visited Sep. 5, 2018 pp. 1-12.

"Document Authentication & Identity Verification Software" https://www.acuantcorp.com/products/assureid-identity-verification-software/ website visited Sep. 5, 2018 pp. 1-10.

"Provide a seamless online experience" https://www.idscan.com/solutions/digital-onboarding/ website visited Sep. 5, 2018 pp. 1-5.

Garrett Gafke "Fraud Prevention Best Practices for On-boarding New Customers" https://payment-and-card.cioreview.com/cxoinsight/fraud-prevention-best-practices-for-onboarding-new-customers-nid-14133-cid-171.html website visited Sep. 5, 2018 pp. 1-7.

"Fueling Growth, Profitability and Security" https://www.threatmetrix.com/cyber-security-solutions/insurance/ website visited Sep. 5, 2018 pp. 1-8.

"How Can AI in the Insurance Industry Help With Fraud Detection and Claims Management" https://www.marutitech.com/ai-in-the-insurance-industry/ website visited Sep. 5, 2018 pp. 1-12.

Ruchi Verma et al. "Using Analyytics for Insurance Fraud Detection" https://www.the-digital-insurer.com/wp-content/uploads/2013/12/53-insurance-fraud-detection.pdf website visited Jan. 2, 2019 pp. 1-10.

"Combat Fraud and Protect Your Bottom Line" Safetech Fraud and Security Solutions PCNP-066 0311 Chase Paymentech Solutions, LLC 2011 pp. 1-6.

"Prevent application fraud and improve customer experience across all channels" Experian https://www.experian.co.uk/identity-and-fraud/fraud-prevention/hunter.html website visited Sep. 5, 2018 pp. 1-5.

"Current fraud trends in the financial sector" Assocham India https://www.pwc.in/assets/pdfs/publications/2015/current-fraud-trends-in-the-financial-sector.pdf Jun. 2015 pp. 1-28.

Jan. 26, 2020—(US) Non-Final Office Action—U.S. Appl. No. 16/238,021.

Feb. 22, 2021—(US) Non-Final Office Action—U.S. Appl. No. 16/238,050.

* cited by examiner

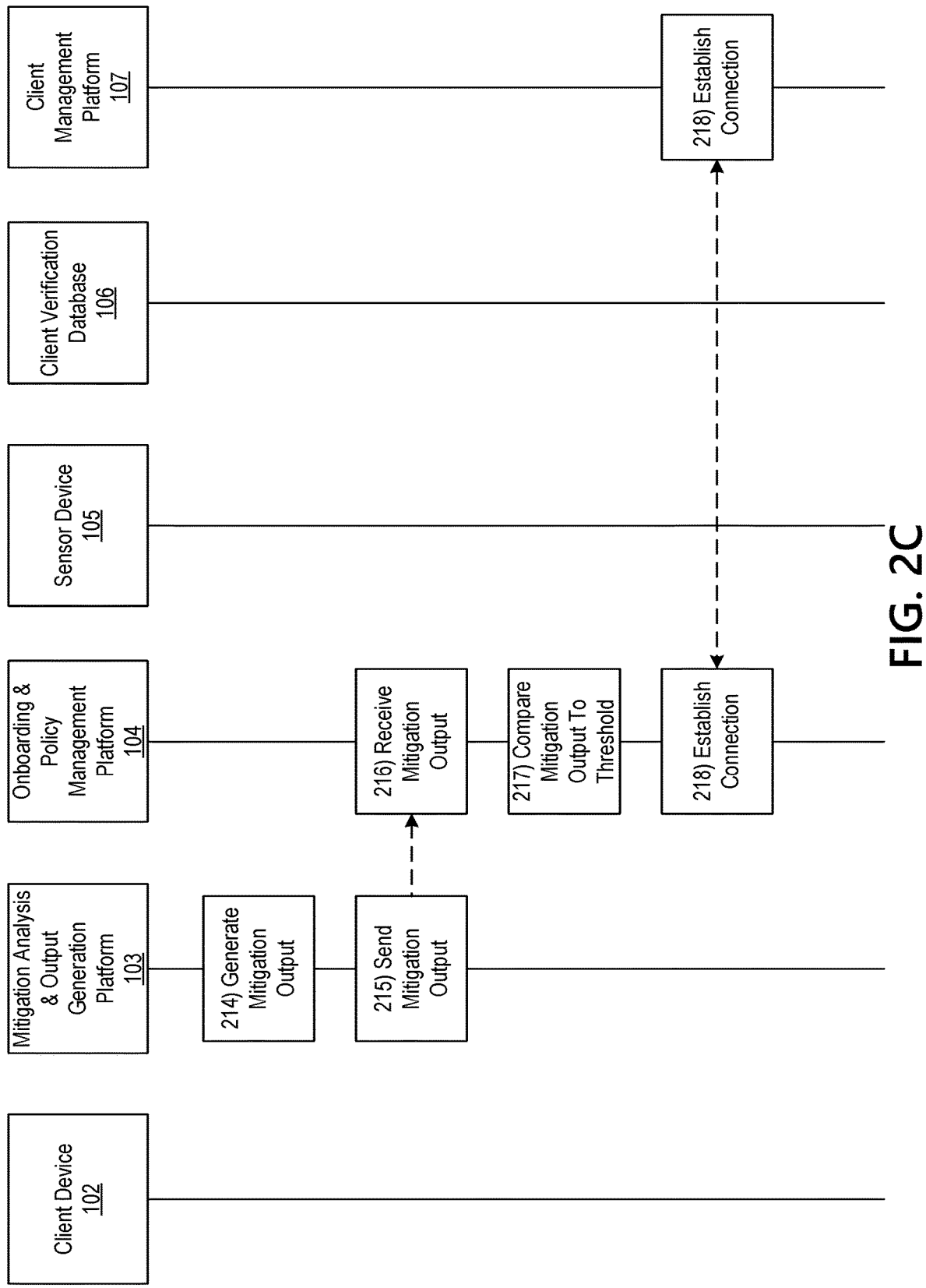

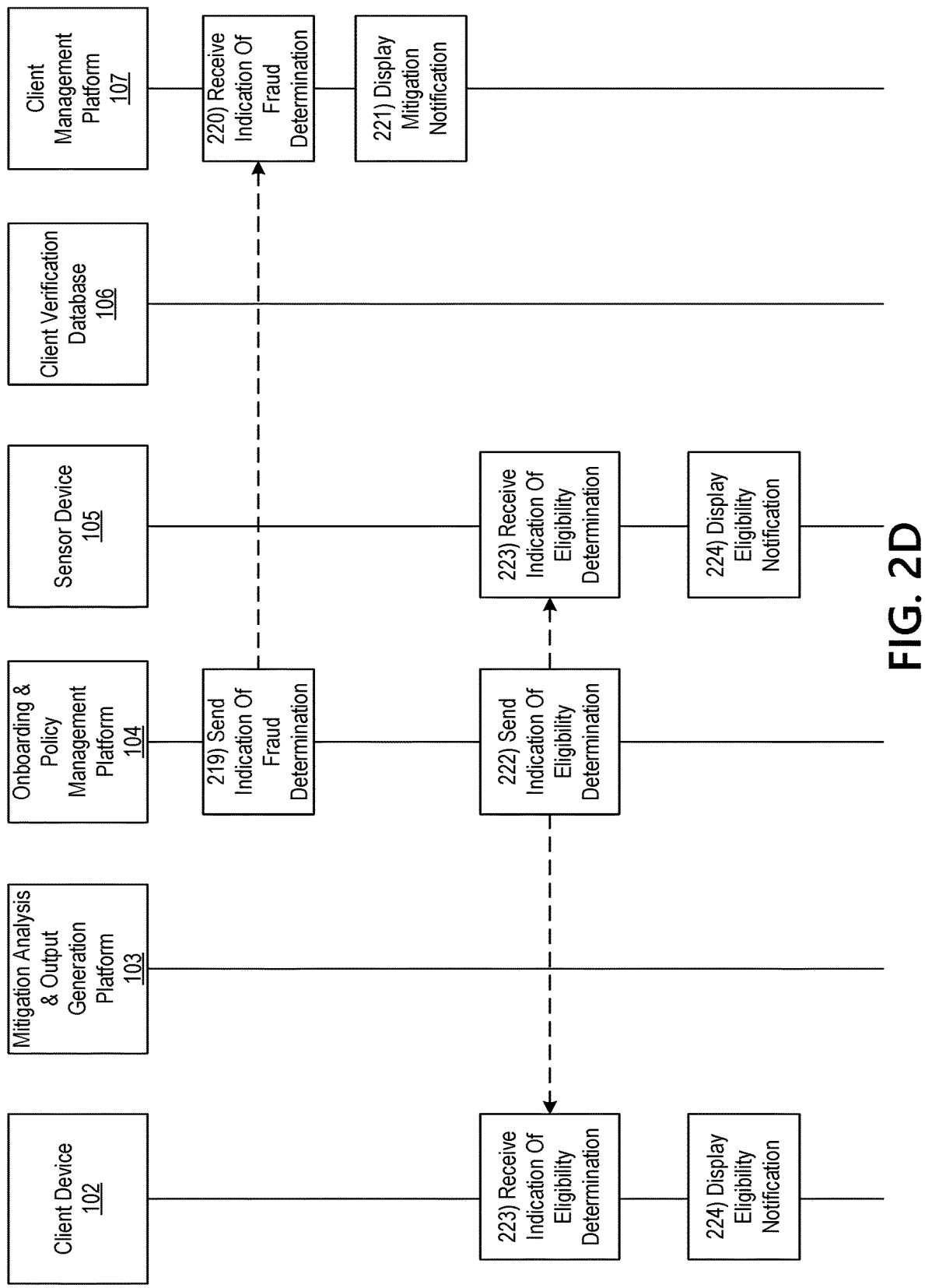

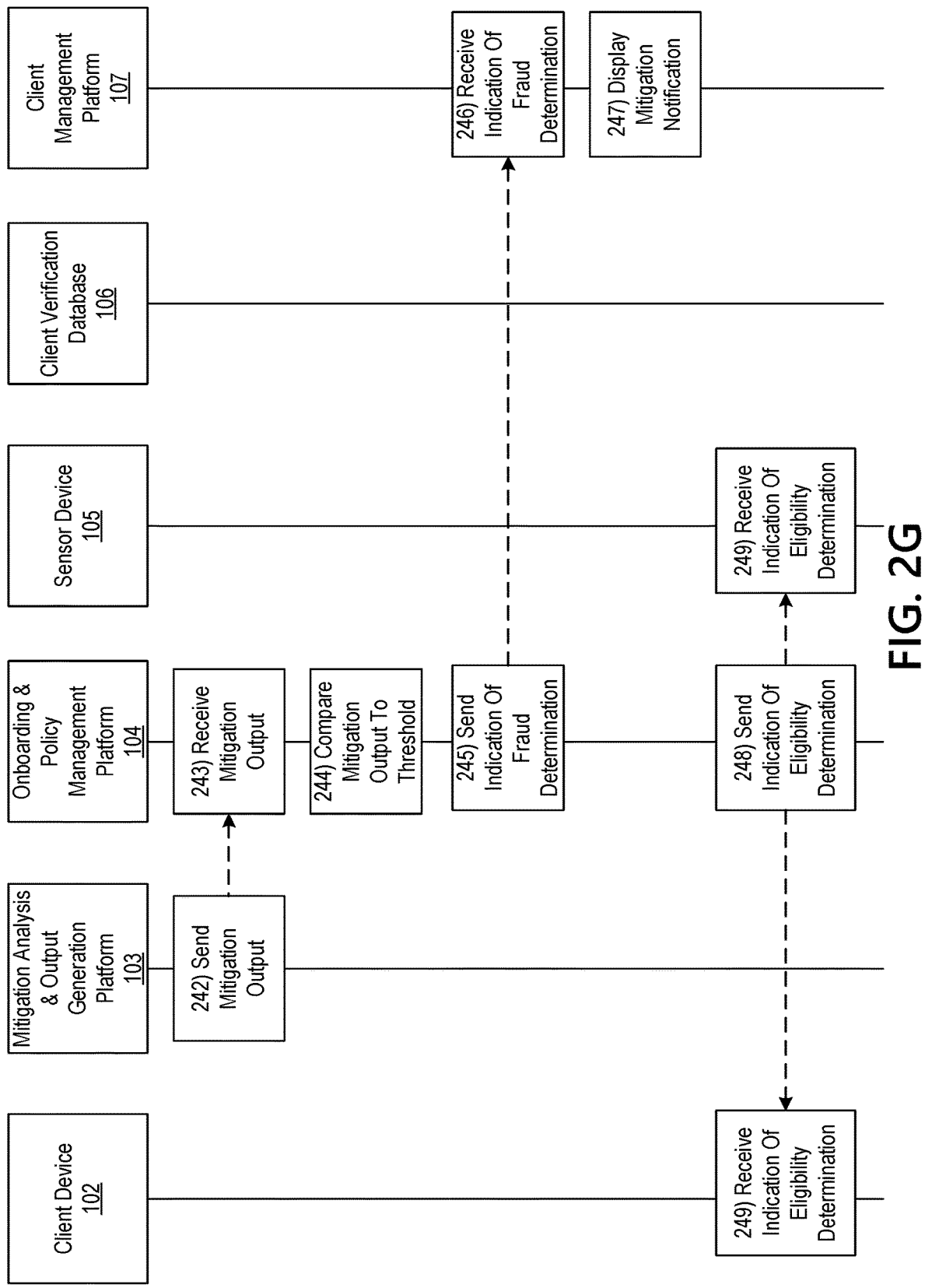

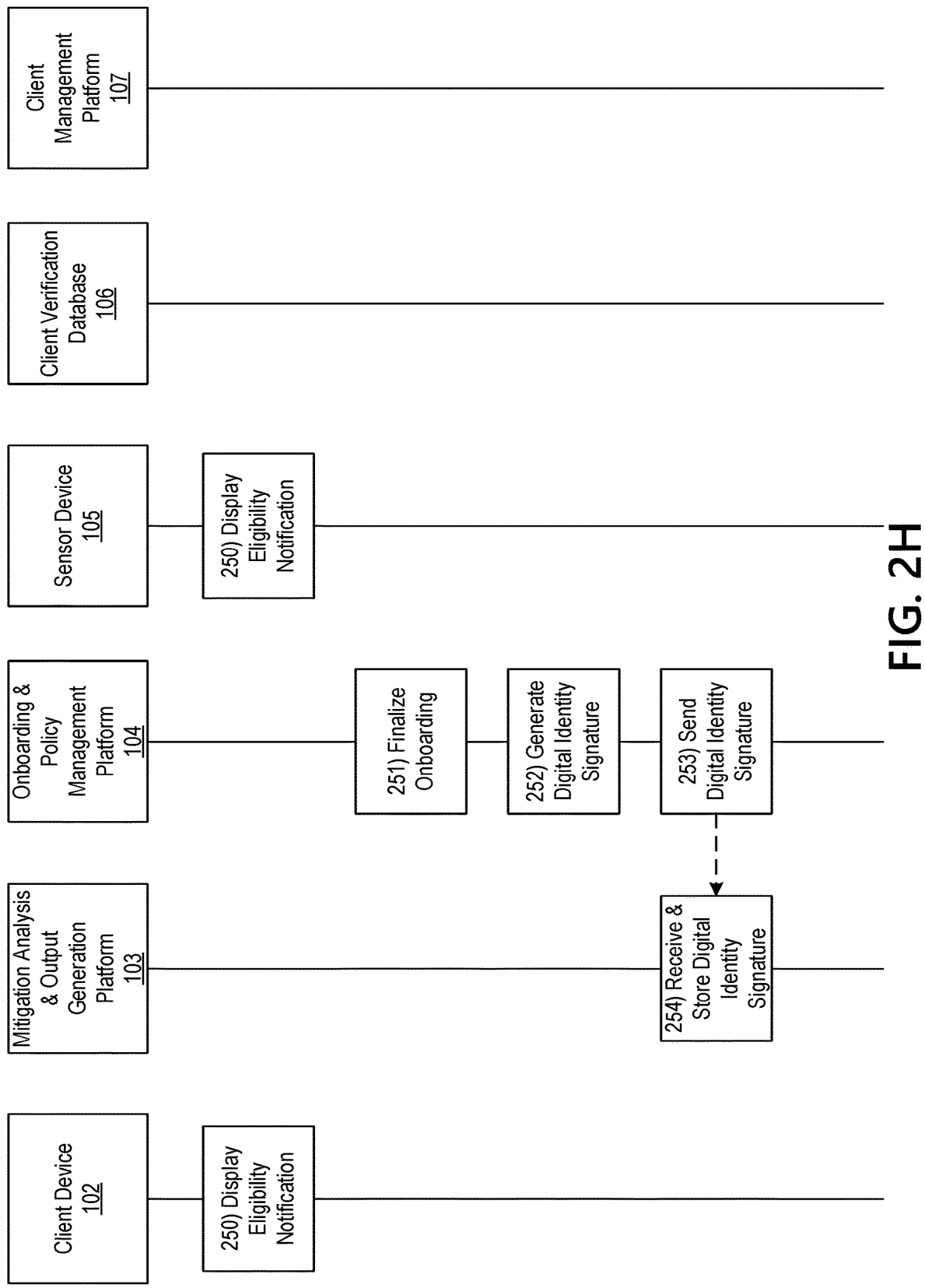

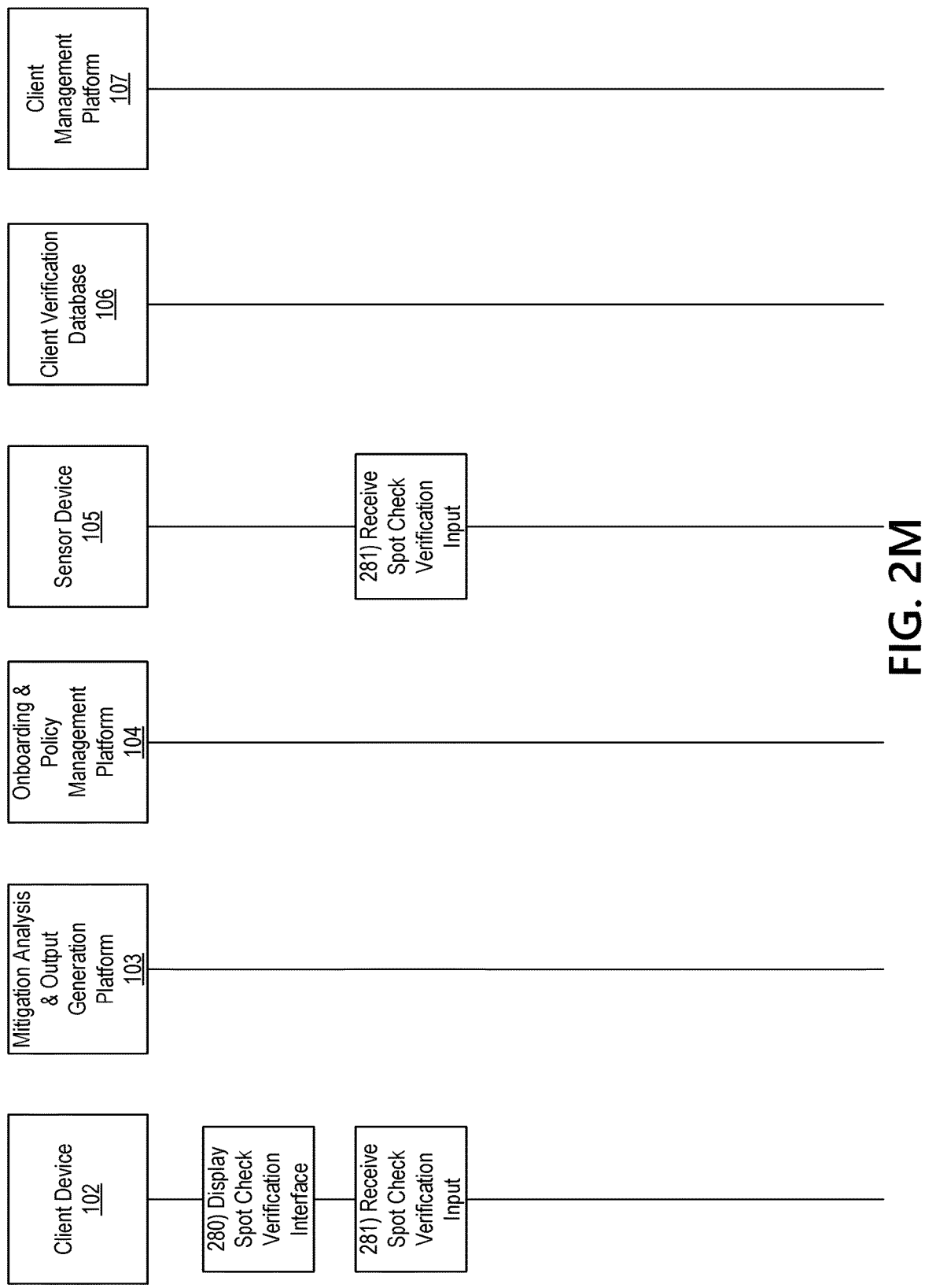

505

Client Onboarding Interface

Welcome to Onboarding!

Please capture an image of a valid photo identification, such as a driver's license or passport, for identity verification.

Client Onboarding Interface

Please capture an image of yourself to confirm your identity.

Client Onboarding Interface

We would like permission to access your electronic health, fitness, and location data.

Cancel　　OK

Client Management Interface

Client X - Onboarding Verification Failure:

A possibility of fraud was detected in the inputs provided by Client X during the onboarding process. Traditional underwriting will be necessary to determine Client X's eligibility for the requested product.

Client Management Interface

Client X - Onboarding Verification Failure:

Fraud was detected in the inputs provided by Client X during the onboarding process. Client X is ineligible for the requested product.

Client Onboarding Interface

An in-person interview will be necessary to determine eligibility for the requested product. Please continue to the next page to schedule an interview.

Cancel          Next Page

Client Onboarding Interface

We regret to notify you that you are ineligible for the requested product. Please contact us at xxx-xxx-xxxx for additional information.

Client Interface

Hello! It has been 90 days since you completed onboarding.

Please select "Accept" below to initiate a spot check verification test.

Accept

Onboarding Management Interface

ALERT: Client failed spot check verification test. Please select next steps.

Additional Test     Terminate Policy

FIG. 8B

ONBOARDING PLATFORM FOR PERFORMING DYNAMIC MITIGATION ANALYSIS

CROSS-REFERENCE TO RELATED APPLICATIONS

This application is a continuation-in-part of and claims priority to U.S. patent application Ser. No. 16/238,050 filed on Jan. 2, 2019, and entitled "Onboarding Platform for Performing Dynamic Mitigation Analysis," and to U.S. patent application Ser. No. 16/238,021 filed on Jan. 2, 2019, and entitled "Onboarding Platform for Performing Dynamic Mitigation Analysis," the contents of each of which is incorporated herein by reference in its entirety.

BACKGROUND

Aspects of the disclosure relate to enhanced processing systems for providing mitigation and spot-check verification outputs using improved methods for analysis of one or more client verification inputs. Many organizations and individuals rely on an onboarding process for purchasing products. In many instances, however, a user identity and other user provided information may be falsified during the onboarding process. There remains an ever-present need to develop alternative solutions to improve client verification during and after the onboarding process.

SUMMARY

Aspects of the disclosure provide effective, efficient, scalable, and convenient technical solutions that address and overcome the technical problems associated with client verification and verification of user-provided information during and after an onboarding process. In accordance with one or more arrangements discussed herein, a computing platform having at least one processor, a communication interface, and memory may determine that a predetermined period of time has elapsed since finalizing an onboarding process. During the onboarding process or in response to determining that the predetermined period of time has elapsed since finalizing the onboarding process, the computing platform may send one or more commands directing a mitigation analysis and output generation platform to analyze and verify the authenticity of user provided information. Additionally or alternatively, in response to determining that the predetermined period of time has elapsed since finalizing the onboarding process, the computing platform may send a spot-check verification notification and one or more commands to display the spot-check verification notification. The computing platform may receive, from the mobile device or other computing device, one or more spot-check verification inputs indicative of a user identity. The computing platform may send one or more commands directing a mitigation analysis and output generation platform to analyze the one or more spot-check verification inputs. The computing platform may receive, from the mitigation analysis and output generation platform, a spot-check verification output indicating a degree of correlation between the one or more received spot-check verification inputs and expected spot-check verification inputs. In response to determining that the spot-check verification output exceeds a predetermined mitigation threshold, the computing platform may send one or more commands directing a client management platform to display a mitigation notification interface, where the mitigation notification interface prompts for user input to void purchase of a product corresponding to the onboarding process or conduct an additional verification test. In response to determining that the additional verification test should be conducted, the computing platform may send mitigation interface information and one or more commands directing the mobile device or other computing device to display a spot-check mitigation interface based on the mitigation interface information, where the spot-check mitigation interface prompts for one or more additional spot-check verification inputs indicative of the user identity.

In some arrangements, the computing platform may determine an amount of time elapsed during the onboarding process. In response to determining that a correlation between the amount of time elapsed during the onboarding process and an expected onboarding process time does not exceed a predetermined onboarding time correlation threshold, the computing platform may void purchase of the product corresponding the onboarding process.

In some examples, the onboarding process may correspond to a process for purchasing the product and wherein the product corresponds to a particular product type. In some arrangements, the computing platform may determine the particular product type. The computing platform may determine the expected onboarding process time based on the particular product type.

In some arrangements, the computing platform may receive from the mitigation analysis and output generation platform, a spot-check verification output indicating a potential fraud scenario. In this case, the mitigation analysis and output generation platform may void the purchase of a product, such as a life (or other type of) insurance program, corresponding to the onboarding process or may raise a fraud alert and prompt for additional processing for the individual to purchase the product.

In some arrangements, the one or more spot-check verification inputs may correspond to one or more onboarding verification inputs received during the onboarding process. In some arrangements, the one or more spot-check verification inputs may correspond to one or more of a pulse/heart rate, a voice signature, a retinal/iris scan, a motion signature, a fingerprint, a code response, global positioning system (GPS) data, a photograph, air sensor data, ambient noise data, acceleration data, and a pressure change.

In some arrangements, the one or more spot-check verification inputs may be received while a video conference session is established between the mobile device and the client management platform. In some arrangements, prior to sending the spot-check verification notification and one or more commands to display the spot-check verification notification, the computing platform may determine that a verified digital identity signature was received. In some arrangements, the one or more commands directing the mitigation analysis and output generation platform to analyze the one or more spot-check verification inputs may direct the mitigation analysis and output generation platform to compare the one or more spot-check verification inputs to verification information from a client verification database.

These features, along with many others, are discussed in greater detail below.

BRIEF DESCRIPTION OF THE DRAWINGS

The present disclosure is illustrated by way of example and not limited in the accompanying figures in which like reference numerals indicate similar elements and in which:

FIGS. 2A-2M depict an illustrative event sequence for deploying computing platforms that utilize improved mitigation analysis and policy management techniques in accordance with one or more example arrangements discussed herein;

FIGS. 5A-5C, 6A-6B, 7A-7B, and 8A-8B depict illustrative user interfaces for computing platforms that utilize improved mitigation analysis and policy management techniques in accordance with one or more example arrangements discussed herein.

DETAILED DESCRIPTION

Figure 1A:
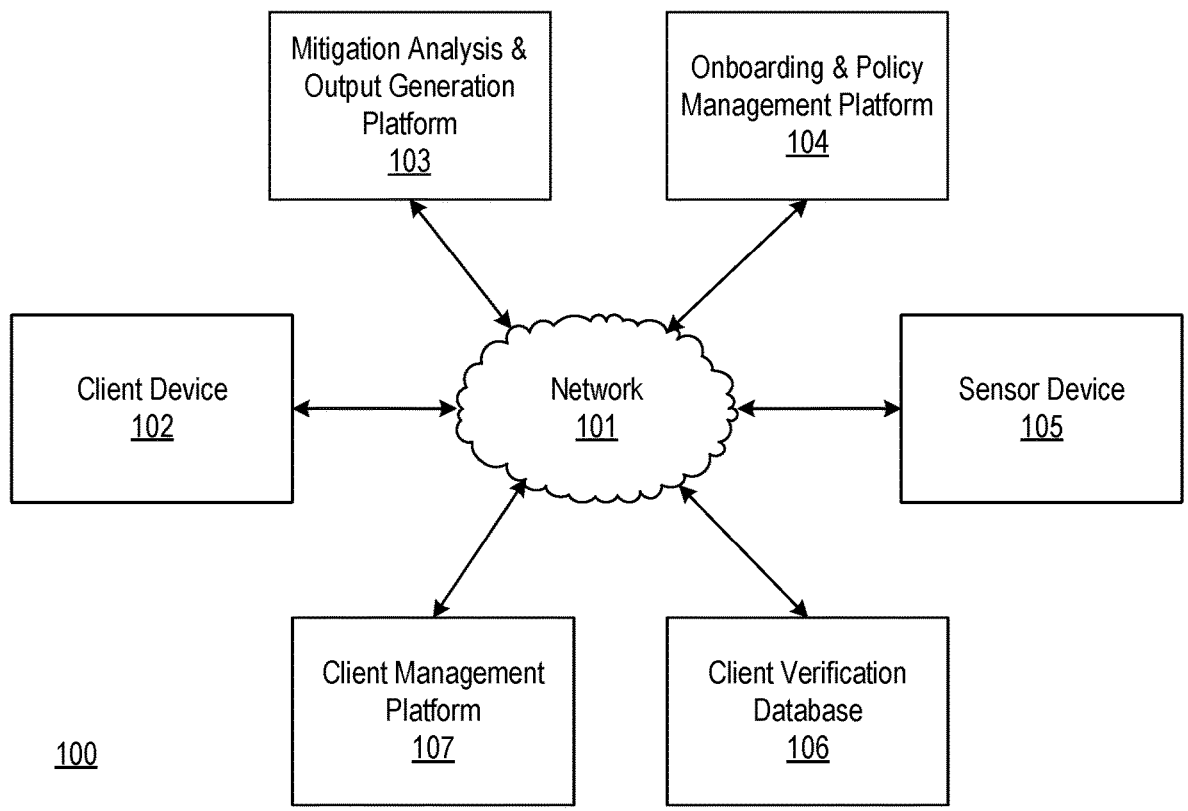
FIGS. 1A-1C depict an illustrative computing environment for deploying computing platforms that utilize improved mitigation analysis and policy management techniques in accordance with one or more example arrangements discussed herein.

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized, and structural and functional modifications may be made, without departing from the scope of the present disclosure.

It is noted that various connections between elements are discussed in the following description. It is noted that these connections are general and, unless specified otherwise, may be direct or indirect, wired or wireless, and that the specification is not intended to be limiting in this respect.

As a brief summary, the present disclosure provides systems and methods for increasing security associated with an onboarding purchasing process. In a particular example, a system may detect potential fraud in the process of an individual signing up for life insurance using their mobile phone or other computer device. To do so, the system may collect information using the mobile phone or other device, such as a wearable fitness device, or may receive information from an external source. This information may be compared to past databases or fraud indicators. If the system detects a potential fraud situation, the system may prevent the user from obtaining the life insurance through an automated process and may prompt for additional actions such as an in-person interview with the individual. The system may also provide a potential fraud score based on analysis of several items of potential fraud analysis. When the score goes above a certain level, the system may prompt for additional processes, such as additional verifications of the individual.

In one or more instances, the system may use one or more sensors on a mobile phone or other device, such as a wearable fitness device, to collect different types of personal information from an individual. For example, a mobile phone and/or other device, such as a wearable fitness device, may capture a location of the device, an image of a person, the person's pulse, a number of steps taken by the person during a period of time, a number of flights climbed by the person during a period of time, a number of minutes the person was active during a period of time, and other personal health-related data. Sensors that may be used may include cameras, voice recorders, accelerometers, altimeters, barometers, gyroscopes, heart rate sensors, GPS sensors, temperature sensors, or the like.

In one or more instances, the system may determine an amount of time that an individual takes to complete an on-boarding process for life or other types of insurance and the complexity of the insurance product purchased. A system may then compare the time for onboarding to pre-set values for fraud detection. If the on-boarding time falls below or above a preset value for a particular type of insurance, then the system may raise a fraud alert and prompt for additional processing for the individual to obtain life (or other types of) insurance.

In one or more instances, the system may engage in a spot-check of a period of time after an individual has obtained life insurance. The system may contact the user at a time that is a surprise to the user (such as through a phone call). The system may prompt the user to provide validating information on the spot. This validating information may include the user's personal fitness/activity data (e.g., pulse, step count, stairs climbed, active minutes, etc.), location information, voice signature, motion signature (e.g., walking, running, or the like), fingerprint, or a response to a ping (a code) from the system. If the validating information does not match expected information, then the system may prompt the individual to engage in additional processes or cancels the insurance policy.

In one or more instances, the system may use virtual assistance in the onboarding process to mitigate fraud. The system may have the user engage in a visual process with a virtual assistant (e.g., a video conference call, or the like). The system may prompt the user to move the phone in certain angles and the remote system may take photos of the user or the background during the visual assistance session. The system may then analyze the information against fraud detectors to validate the identity of the user and to ensure that no one else, such as a healthier person, is providing information during the onboarding process. For example, the system may compare the photos of the user during the video assistance session to other photos previously taken as part of the onboarding process or to other photos taken during the same virtual assistance session. The photos may be compared using various image processing techniques. If the system determines that differences above a threshold level exist between the photos, the system may prompt for additional processing.

In one or more instances, the system may analyze a user's identifying information or other user-provided information during a contestability period. The system may determine if the identifying or other information falls within certain fraud detection parameters and if so, the system may prompt for additional fraud mitigation steps such as an in-person interview or cancellation of the policy. As one example, the system may determine if the information provided during the contestability period matches the information provided during the on-boarding process. Information that may be obtained and analyzed during the contestability period may include GPS data, photos, air sensor data, ambient noise data, heart rate data, personal fitness/activity data, accelerometer data, pressure change data, movement signatures, or the like.

These and various other arrangements will be described more fully herein.

Figure 1B:
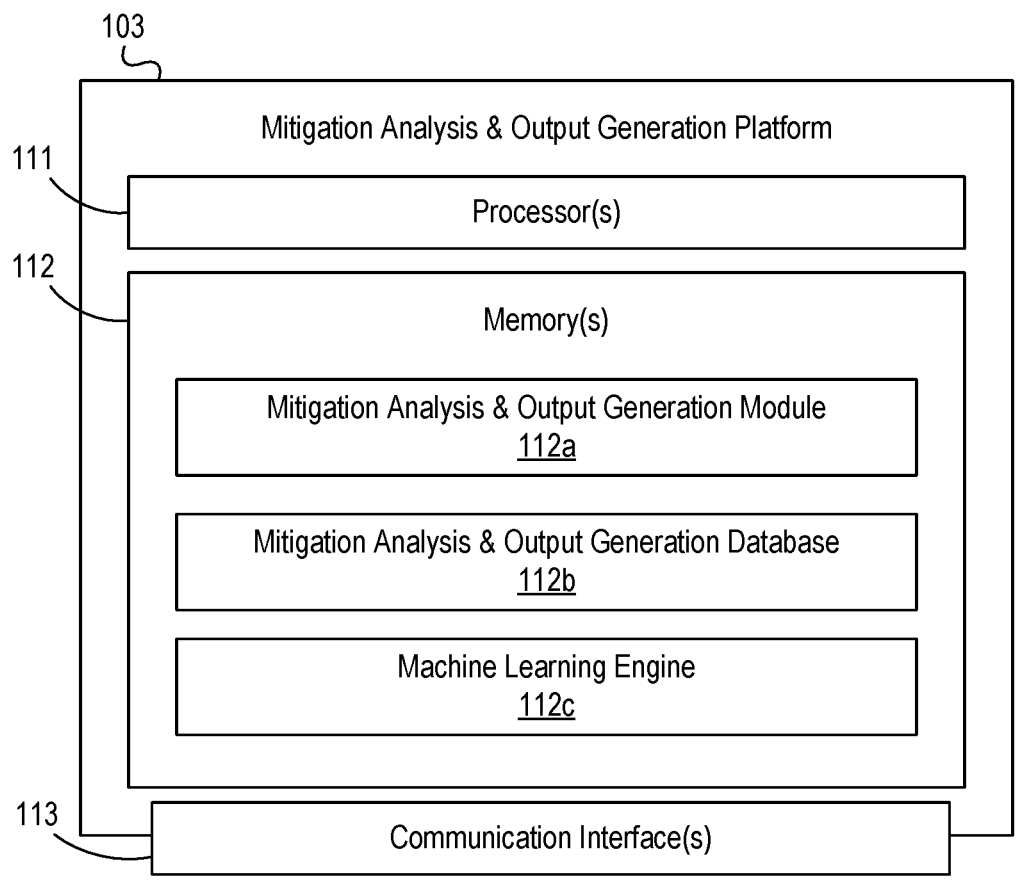
Figure 1C:
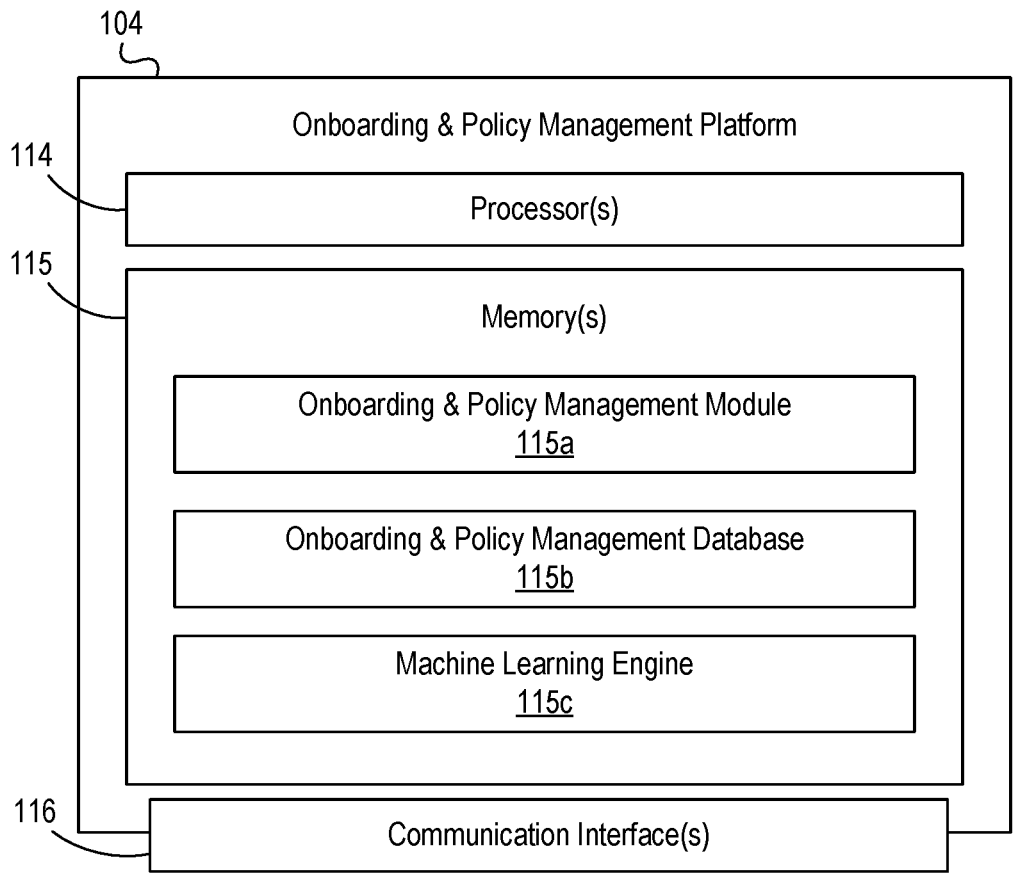

FIGS. 1A-1C depict an illustrative computing environment for deploying an onboarding policy and management platform that causes performance of advanced mitigation analysis techniques in accordance with one or more example embodiments. Referring to FIG. 1A, computing environment 100 may include one or more computer systems. For example, the computing environment 100 may include client device 102, mitigation analysis and output generation platform 103, onboarding policy and management platform 104, sensor device 105, client verification database 106, and client management platform 107.

The client device 102 may be a personal computing device (e.g., smartphone, laptop computer, desktop computer, tablet computer, wearable fitness device, a smart watch, or the like) that is capable of receiving commands and generating user interfaces accordingly. In addition, the client device 102 may include one or more cameras and/or sensors (e.g., motion sensors, GPS sensors, temperature sensors, microphones, cameras, voice recorders, accelerometers, altimeters, barometers, gyroscopes, heart rate sensors, GPS sensors, or the like) that may be used to capture data corresponding to a user. In some instances, the client device 102 may be configured to send this data upon request or at predetermined intervals for analysis.

As illustrated in greater detail below, the mitigation analysis and output generation platform 103 may include one or more computing devices configured to perform one or more of the functions described herein. For example, mitigation analysis and output generation platform 103 may include one or more computers (e.g., laptop computers, desktop computers, servers, server blades, or the like). In one or more instances, mitigation analysis output generation platform 103 may be configured to receive data captured by the client device 102 and/or the sensor device 105 and analyze the data to determine mitigation outputs. In one or more instances, the mitigation analysis and output generation platform 103 may have access to data stored at the client verification database 106, and may compare the data from the client device 102 and/or the sensor device 105 to the data stored at the client verification database 106 to determine the mitigation outputs.

As illustrated in greater detail below, the onboarding policy and management platform 104 may be configured to generate, host, transmit, and/or otherwise provide one or more web pages and/or other graphical user interfaces (which may, e.g., cause one or more other computer systems to display and/or otherwise present the one or more web pages and/or other graphical user interfaces). In some instances, the web pages and/or other graphical user interfaces generated by onboarding policy and management platform 104 may be associated with an external portal provided by an organization, such as an onboarding portal provided by an insurance institution or provider that may allow customers to purchase insurance products. Although FIG. 1A depicts the mitigation analysis and output generation platform 103 and the onboarding policy and management platform 104 as two distinct computing devices, it should be understood that in some instances, the mitigation analysis and output generation platform 103 and the onboarding policy and management 104 may be implemented in a single computing platform.

The sensor device 105 may be a computing device configured to collect and send data for further analysis. In some instances, the sensor device 105 may be a fitness tracker or other wearable device, a microphone, a heart rate monitor, an accelerometer, a pressure sensor, a movement sensor, other health sensor, or the like. It should be understood that in some instances, the sensor 105 may be embedded in the client device 102.

The client verification database 106 may be a computing platform capable of storing and maintaining various information corresponding to one or more clients. For example, the client verification database 106 may contain fitness/activity data, health data, gait pattern biometrics data (e.g., data identifying individuals based on their walking patterns, or the like), a voice signature, a facial signature, an iris scan, a security question and response/code, a date of birth, a social security number, a home address, movement data, photographs, personal fitness/activity data (e.g., pulse, step count, stairs climbed, active minutes, etc.), email addresses associated with the client, account numbers of accounts associated with the client, or the like corresponding to the clients. In one or more instances, the client verification database 106 may be configured to receive requests for the information corresponding to a particular client, identify the information corresponding to the particular client, and send the information for the particular client. In one or more instances, the client verification database 106 may be an internal database associated with an institution (e.g., an insurance institution). In other instances, the client verification database 106 may be an external database associated with a third party (e.g., a social media database, an electronic health records (EHR) database, an electronic health records aggregator database, an inter-insurer database or clearinghouse containing the identifications if known fraudsters, or the like).

The client management platform 107 may be a computing device (e.g., a desktop computer, laptop computer, tablet computer, smart phone, or the like) that may be used to receive mitigation notifications and display user interfaces accordingly. For example, the client management platform 107 may be used by an employee of an insurance institution to determine a potential security threat associated with purchase of a particular insurance product. Accordingly, the client management platform 107 may receive user input from the employee indicating whether the purchase should be voided or whether additional client verification tests should be performed.

The computing environment 100 also may include one or more networks, which may interconnect one or more of client device 102, mitigation analysis and output generation platform 103, onboarding and policy management platform 104, sensor device 105, client verification database 106, and client management platform 107. For example, computing environment 100 may include a network 101 (which may, e.g., interconnect dynamic client device 102, mitigation analysis and output generation platform 103, onboarding and policy management platform 104, sensor device 105, client verification database 106, and client management platform 107).

In one or more arrangements, the client device 102, the mitigation analysis and output generation platform 103, the onboarding and policy management platform 104, the sensor device 105, the client verification database 106, the client management platform 107, and/or the other systems included in the computing environment 100 may be any type of computing device capable of receiving a user interface, receiving input using the user interface, and communicating the received input to one or more other computing devices. For example, the client device 102, the mitigation analysis and output generation platform 103, the onboarding and policy management platform 104, the sensor device 105, the client verification database 106, the client management platform 107, and/or the other systems included in the computing environment 100 may, in some instances, be and/or include server computers, desktop computers, laptop computers, tablet computers, smart phones, or the like that may include one or more processors, memories, communication interfaces, storage devices, and/or other components. As noted above, and as illustrated in greater detail below, any and/or all of the client device 102, the mitigation analysis and output generation platform 103, the onboarding and policy management platform 104, the sensor device 105, the client verification database 106, and the client management platform 107 may, in some instances, be special-purpose computing devices configured to perform specific functions.

Referring to FIG. 1B, the mitigation analysis and output generation platform 103 may include one or more processors 111, memory 112, and communication interface 113. A data bus may interconnect the processor 111, the memory 112, and the communication interface 113.

The communication interface 113 may be a network interface configured to support communication between the mitigation analysis and output generation platform 103 and one or more networks (e.g., network 101, or the like).

The memory 112 may include one or more program modules having instructions that, when executed by the processor 111, cause the mitigation analysis and output generation platform 103 to perform one or more functions described herein and/or may include one or more databases that may store and/or otherwise maintain information which may be used by such program modules and/or the processor 111. In some instances, the one or more program modules and/or databases may be stored by and/or maintained in different memory units of the mitigation analysis and output generation platform 103 and/or by different computing devices that may form and/or otherwise make up the mitigation analysis and output generation platform 103. For example, the memory 112 may have, store, and/or include a mitigation analysis and output generation module 112a, a mitigation analysis and output generation database 112b, and a machine learning engine 112c.

The mitigation analysis and output generation module 112a may include instructions that direct and/or cause the mitigation analysis and output generation platform 103 to execute advanced computer vision methods for analyzing onboarding and spot-check verification inputs and generating mitigation outputs, as discussed in greater detail below.

The mitigation analysis and output generation module 112b may store information used by the mitigation analysis and output generation module 112a and/or the mitigation analysis and output generation platform 103 in onboarding and spot-check verification input analysis, mitigation output generation, and/or in performing other functions.

The machine learning engine 112c may include instructions that direct and/or cause the mitigation analysis and output generation platform 103 to perform onboarding and spot-check verification analysis and to set, define, and/or iteratively refine optimization rules and/or other parameters used by the mitigation analysis and output generation platform 103 and/or other systems in the computing environment 100.

Referring to FIG. 1C, the onboarding and policy management platform 104 may include one or more processors 114, memory 115, and communication interface 116. A data bus may interconnect the processor 114, the memory 115, and the communication interface 116.

The communication interface 116 may be a network interface configured to support communication between the onboarding and policy management platform 104 and one or more networks (e.g., network 101, or the like).

The memory 115 may include one or more program modules having instructions that, when executed by the processor 114, cause the onboarding and policy management platform 104 to perform one or more functions described herein and/or may include one or more databases that may store and/or otherwise maintain information which may be used by such program modules and/or the processor 114. In some instances, the one or more program modules and/or databases may be stored by and/or maintained in different memory units of the onboarding and policy management platform 104 and/or by different computing devices that may form and/or otherwise make up the onboarding and policy management platform 104. For example, the memory 115 may have, store, and/or include an onboarding and policy management module 115a, an onboarding and policy management database 115b, and a machine learning engine 115c.

The onboarding and policy management module 115a may include instructions that direct and/or cause the onboarding and policy management platform 104 to execute onboarding and policy management methods for analyzing an onboarding process and determining whether satisfactory client identification has been performed and whether satisfactory client information has been provided, as discussed in greater detail below.

The onboarding and policy management database 115b may store information used by the onboarding and policy management module 115a and/or the onboarding and policy management platform 104 in onboarding analysis and/or in performing other functions.

The machine learning engine 115c may include instructions that direct and/or cause the onboarding and policy management platform 104 to perform onboarding and policy management, and to set, define, and/or iteratively refine optimization rules, algorithms, and/or other parameters used by the onboarding and policy management platform 104 and/or other systems in the computing environment 100.

FIGS. 2A-2M depict an illustrative event sequence for deploying the mitigation analysis and output generation platform 103 and the onboarding and policy management platform 104, which utilize advanced methods and techniques to perform fraud analysis during and after an onboarding purchasing process to perform client identity verification and mitigate security threats in accordance with one or more example embodiments.

Figure 2A:
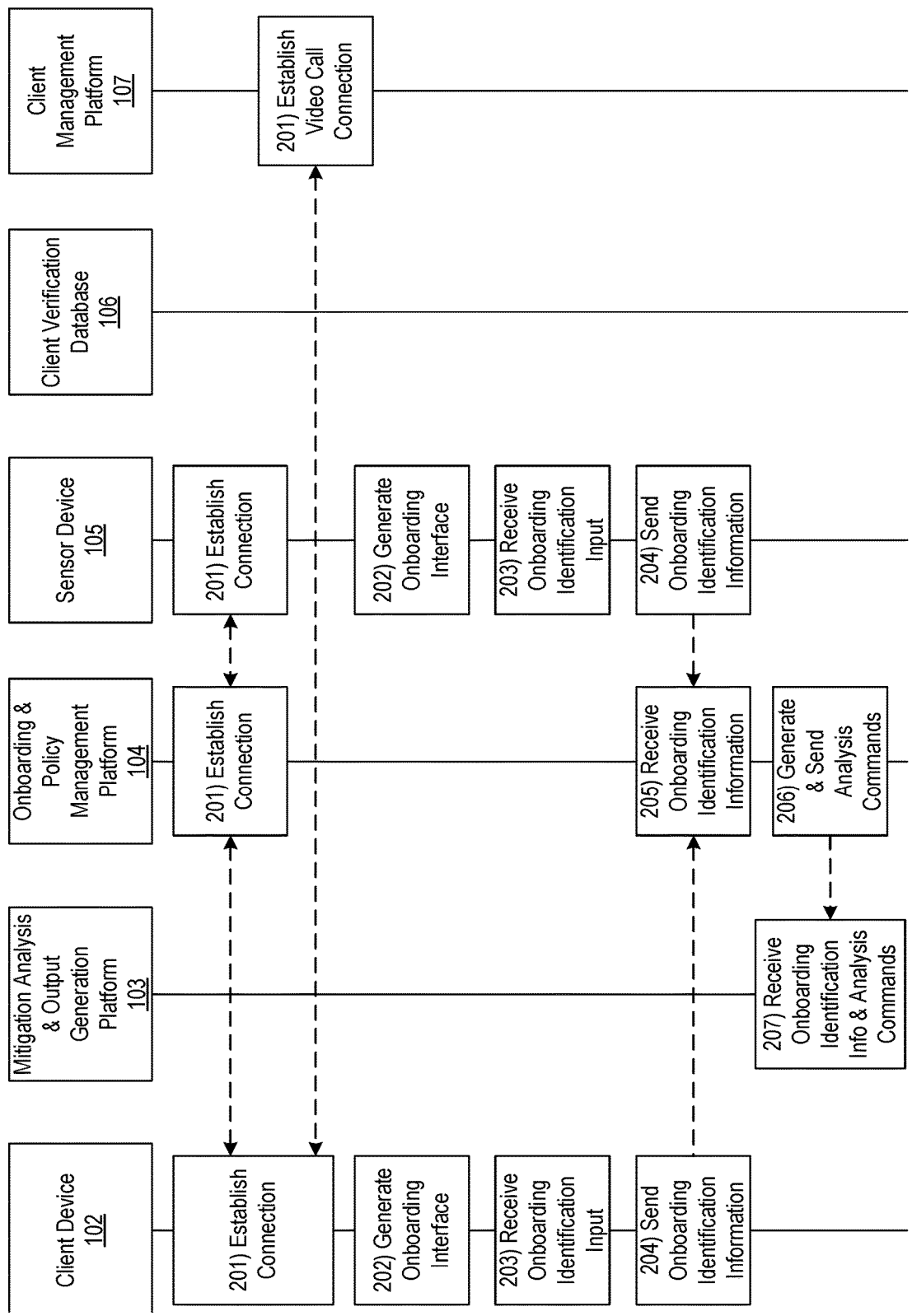

Referring to FIG. 2A, at step 201, the client device 102 and the sensor device 105 may establish connections with the onboarding and policy management platform 104. In one or more instances, the client device 102 and the sensor device 105 may establish first and second wireless data connections to the onboarding and policy management platform 104 to link the client device 102 and the sensor device 105, respectively, to the onboarding and policy management platform 104. Additionally or alternatively, the client device 102 may establish a video call connection with the client management platform 107.

At step 202, the client device 102 and/or the sensor device 105 may generate and display a client onboarding interface for receiving onboarding inputs. For example, a client may be interested in purchasing one or more products through an external portal provided by an institution (e.g., insurance products provided by an insurance institution). In one or more instances, the client device 102 and/or the sensor device 105 may display the client onboarding interface for the purpose of allowing a client to purchase a product (e.g., an insurance policy or the like). In these instances, onboarding inputs received at the client device 102 and/or sensor device 105 may be used by the onboarding and policy management platform 104 to determine whether the client is eligible to purchase one or more types of the product (e.g., life insurance, home insurance, vehicle insurance, or the like). The onboarding inputs may include inputs by the client specifying the type of product the client is interested in purchasing, e.g., life insurance, home insurance, vehicle insurance, etc., and coverage amounts requested for the product. The onboarding inputs may further include onboarding identification inputs provided for the purpose of establishing the client's identity, health inputs provided for the purpose of establishing one or more aspects of the client's health and fitness/activity, location inputs provided for the purpose of establishing movement patterns of the client, and/or other inputs provided for further establishing the client's eligibility for the requested product. These inputs may be used alone, or with other information, to make a determination regarding the client's eligibility for purchasing the product. In one or more instances, in displaying the client onboarding interface, the client device 102 or sensor device 105 may generate and display a graphical user interface similar to graphical user interface 505, which is shown in FIG. 5A. For example, the client device 102 may welcome a client to the onboarding process, and may indicate a method of identity verification.

At step 203, the client may provide user input, using the client device 102, the sensor device 105, or both, to confirm his or her identity. For example, the client device 102 or the sensor device 105 may be used to capture an image of a client identification document, such as a passport or driver's license, which identifies the client's name, address, date of birth, gender, etc.

In order to verify that the provided client identification document belongs to the client performing the onboarding process, the system may require additional identification information to confirm the client's identity. In this case, the process may return to step 202, and the client device 102 or the sensor device 105 may generate and display a graphical user interface similar to graphical user interface 510, which is shown in FIG. 5B. For example, the client device 102 may request that the client provide one or more additional identification inputs, such as capturing an image of the client, to confirm the client's identity.

In this case, the process may proceed again to step 203, and the client device 102 or the sensor device 105 may receive one or more onboarding identification inputs as confirmation of the client identification document (e.g., a passport, driver's license, or the like), e.g., a fingerprint, a facial signature (e.g., using facial recognition), retina/iris biometrics, a voice signature (e.g., several words or a phrase spoken by a user of the client device 102), a signature based on GPS data (e.g., a typical trip to work in the morning, a region in which the client device 102 is typically used, or the like), a video/image/photograph of the user, an international mobile equipment identity (IMEI) number of the client device 102, a usage signature for the client device 102 (e.g., typical call/text patterns or the like), a pulse of the user, a number of phone usages, fitness data, blood pressure data, blood sugar data, activity data, body mass index (BMI) data, body fat data, maximum oxygen consumption data, or the like. In one or more instances, the client device 102 and the sensor device 105 may both receive onboarding identification inputs. In other instances, only one of the client device 102 or the sensor device 105 may receive onboarding identification inputs. In one or more instances, the client device 102 and/or the sensor device 105 may receive the onboarding identification inputs at a single sensor. In other instances, the client device 102 and/or the sensor device 105 may receive the onboarding identification inputs using multiple sensors. For example, the client device 102 and/or the sensor device 105 may detect two different types of personal information from the client (e.g., an image of the client and the client's pulse, an image of the client and a blood pressure/sugar measurement of the client, an image of the client and the client's voice signature, an image of the client and the client's fingerprint, or the like).

In one or more instances, while the onboarding identification inputs are being received, microphones on the client device 102 and/or the sensor device 105 may be used to determine if the alleged client is being coached through the onboarding identification input process. Additionally or alternatively, while the onboarding identification inputs are being received, infrared sensors, image sensors, or other sensor devices, may be used to detect whether the alleged client is alone, or whether additional individuals are present. Both of these techniques may provide information that may be beneficial to the mitigation analysis and output generation platform 103 in its analysis at step 212.

At step 204, the client device 102 and the sensor device 105 may generate and send onboarding identification information (corresponding to the onboarding identification inputs received at step 203) to the onboarding policy management platform 104. In sending the onboarding identification information, the client device 102 and the sensor device 105 may send the onboarding identification information while the first and second wireless data connections, respectively, are established.

At step 205, the onboarding and policy management platform 104 may receive the onboarding identification information sent at step 204. In one or more instances, the onboarding and policy management platform 104 may receive the onboarding identification information via the communication interface 116 and while the first and second wireless data connections are established. In one or more instances, in receiving the onboarding identification information, the onboarding and policy management platform 104 may determine an amount of time elapsed since initiation of the onboarding process.

At step 206, the onboarding and policy management platform 104 may generate and send one or more commands directing the mitigation analysis and output generation platform 103 to analyze the onboarding identification information. In one or more instances, the onboarding and policy management platform 104 may establish a wireless data connection with the mitigation analysis and output generation platform 103. For example, the onboarding and policy management platform 104 may establish a third wireless data connection with the mitigation analysis and output generation platform 103 to link the onboarding and policy management platform 104 to the mitigation analysis and output generation platform 103. In these instances, the onboarding and policy management platform 104 may send, via the communication interface 116 and while the third wireless data connection is established, the one or more commands directing the mitigation analysis and output generation platform 103 to analyze the onboarding identification information. In one or more instances, the onboarding and policy management platform 104 may send the one or more commands directing the mitigation analysis and output generation platform 103 to analyze the onboarding identification information along with the onboarding identification information.

At step 207, the mitigation analysis and output generation platform 103 may receive the onboarding identification information and the one or more commands directing the mitigation analysis and output generation platform 103 to analyze the onboarding identification information. In one or more instances, the mitigation analysis and output generation platform 103 may receive, via the communication interface 113 and while the third wireless data connection is established, the onboarding identification information and the one or more commands directing the mitigation analysis and output generation platform 103 to analyze the onboarding identification information.

Figure 2B:
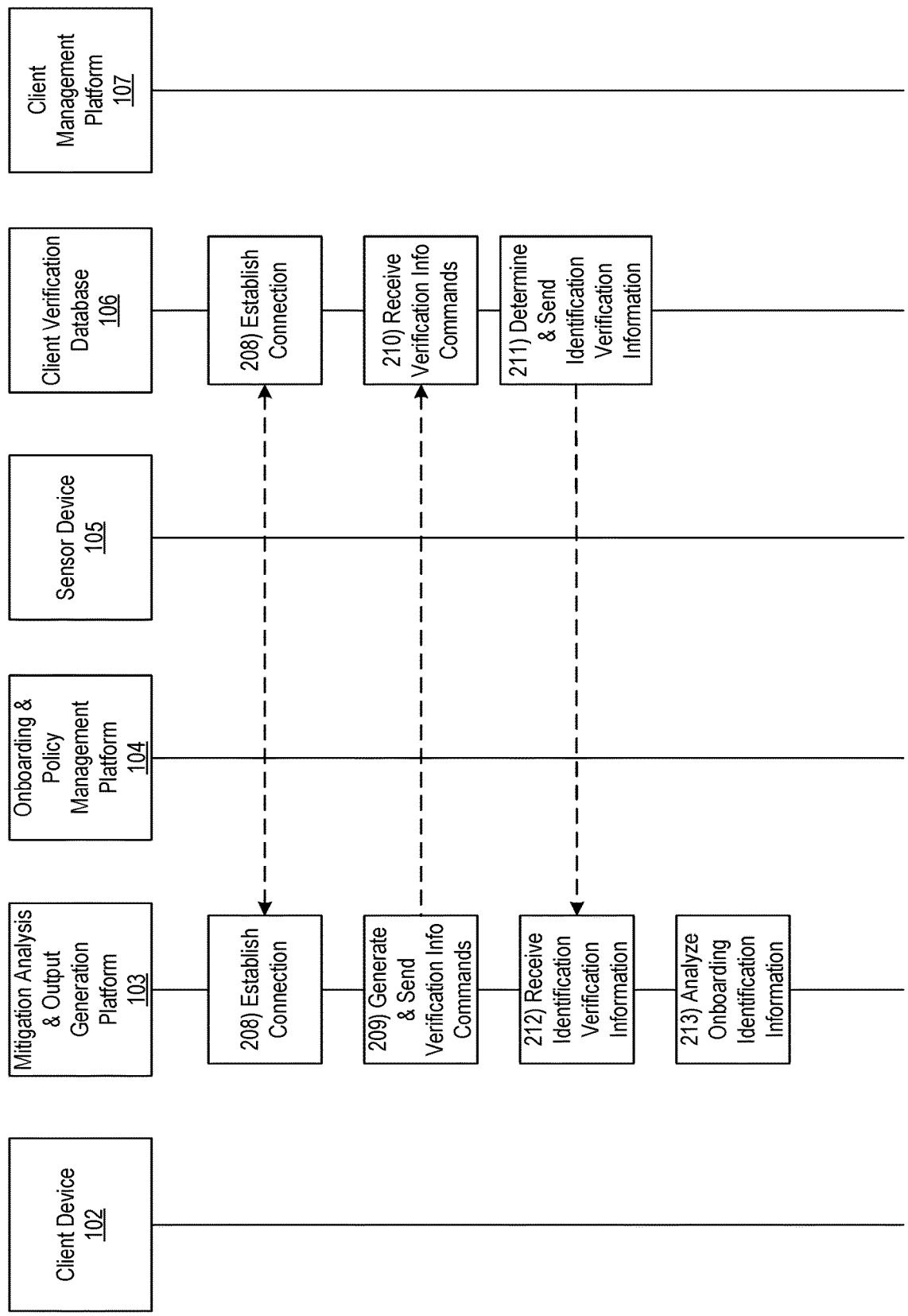
Figure 2E:
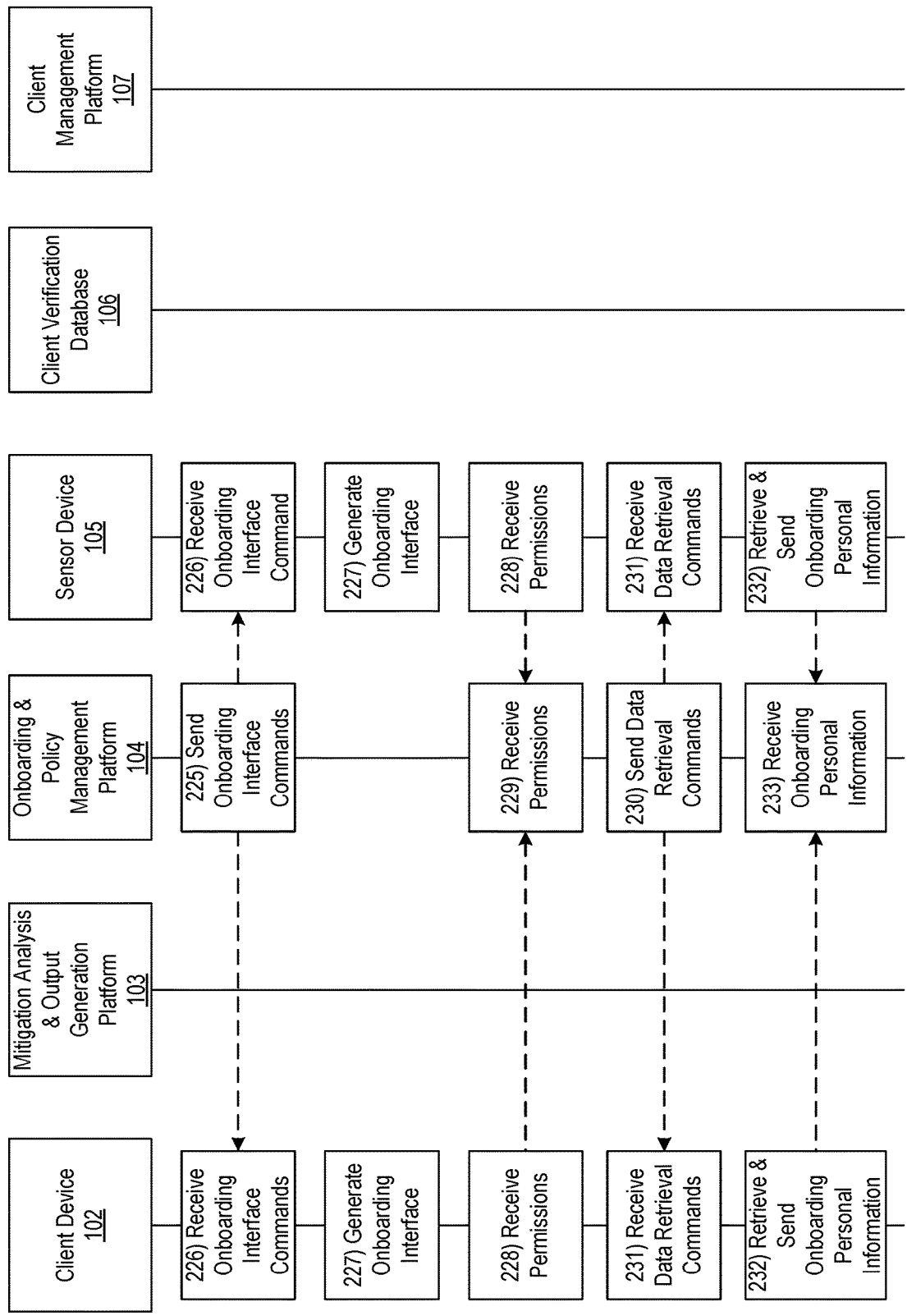
Figure 2F:
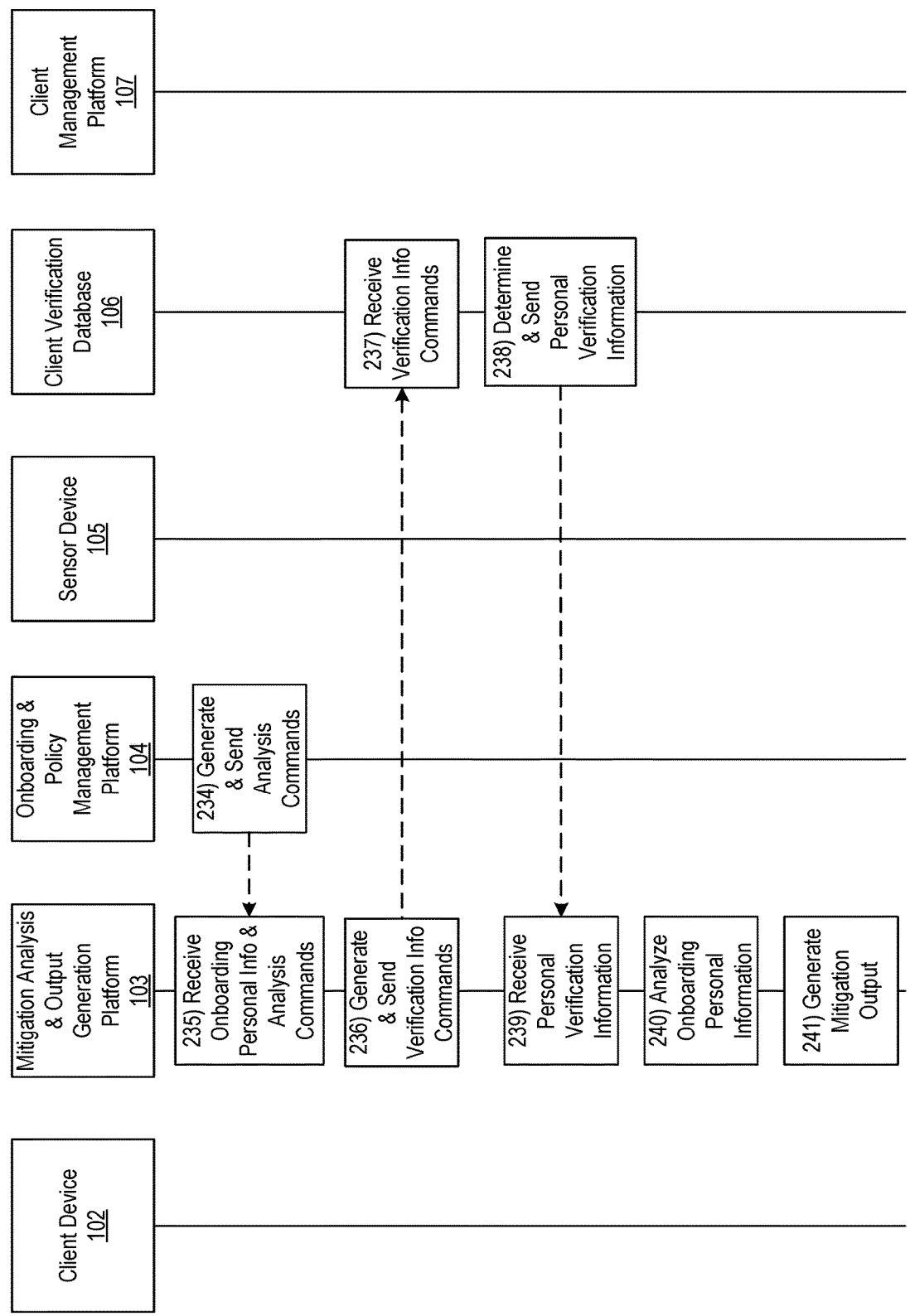

Referring to FIG. 2B, at step 208, the mitigation analysis and output generation platform 103 may establish a connection with the client verification database 106. In one or more instances, the mitigation analysis and output generation platform 103 may establish a fourth wireless data connection with the client verification database 106 to link the mitigation analysis and output generation platform 103 to the client verification database 106.

At step 209, the mitigation analysis and output generation platform 103 may generate one or more commands directing the client verification database 106 to determine client identification verification information and may send the commands to the client verification database 106. In one or more instances, the mitigation analysis and output generation platform 103 may send, via the communication interface 113 and while the fourth wireless data connection is established, the one or more commands directing the client verification database 106 to determine the client identification verification information.

At step 210, the client verification database 106 may receive the one or more commands, that were sent at step 209, directing the client verification database 106 to determine the client identification verification information. In one or more instances, the client verification database 106 may receive the one or more commands directing the client verification database 106 to determine the client identification verification information while the fourth wireless data connection is established.

At step 211, the client verification database 106 may determine client identification verification information corresponding to the client who allegedly provided the onboarding identification input at step 203. In one or more instances, the client verification database 106 may maintain data corresponding to each client of an institution corresponding to the onboarding and policy management platform 104 (e.g., an insurance institution). The client verification database 106 may maintain a database of client identifiers corresponding to various client devices and sensor devices, and may also maintain stored data previously received from each of these client and sensor devices. Accordingly, the client verification database 106 may maintain data that may be used as a reference point (e.g., compared against the onboarding identification information) to verify that an owner of the client device 102 or sensor device 105 is the one providing the onboarding identification inputs. This may prevent clients from, for example, having a friend or other individual, who is healthier (e.g., has a lower resting heart rate, has lower blood pressure, or the like) than the actual user requesting the product or service, from providing onboarding identification inputs, such as exercise data, pulse, or the like, to get a better premium, better discounts, etc. on the requested insurance product. In one or more instances, the client verification database 106 may obtain the client identification verification information via user input from the clients themselves. Additionally or alternatively, the client verification database 106 may access one or more internal or external databases to obtain the client identification verification information.

In one or more instances, the client verification database 106 may maintain client identification documents (e.g., a passport, driver's license, or the like), a fingerprint, a social security number, a date of birth, a response/code of a security question, a current home address, an iris/retina scan, a facial signature (e.g., using facial recognition), a voice signature (e.g., several words or a phrase spoken by a user of the client device 102), a signature based on GPS data (e.g., a typical trip to work in the morning, a region in which the client device 102 is typically used, or the like), a video of the user, an IMEI number or other identifier of the client device 102, a usage signature for the client device 102 (e.g., typical call/text patterns or the like), a number of phone usages, personal fitness/activity data (e.g., pulse, step count, stairs climbed, active minutes, etc.), location information, email addresses associated with the client, account numbers of accounts associated with the client, or the like. In one or more instances, the client verification database 106 may maintain social media data (e.g. pictures stored on social media, mined information from social media regarding engagement in risky avocations/aviation (e.g., mountain climbing, vehicle racing, sky diving, scuba diving, aircraft flying, hang gliding, heli-skiing, or the like) or the like). In one or more instances, the client verification database 106 may be an internal database associated with an institution (e.g., an insurance institution). In other instances, the client verification database 106 may be an external database associated with a third party (e.g., a social media database, an EHR database, an electronic health records aggregator database, an inter-insurer database or clearinghouse containing the identifications if known fraudsters, or the like).

Once the client verification database 106 determines the client identification verification information corresponding to the alleged client (e.g., by indexing a device identifier of the client device 102 and/or sensor device 105 to determine a user identifier corresponding to the device, and subsequently indexing the user identifier to determine the relevant client identification verification information), the client verification database 106 may send the relevant client identification verification information to the mitigation analysis and output generation platform 103. In one or more instances, the client verification database 106 may send the client identification verification information to the mitigation analysis and output generation platform 103 while the fourth wireless data connection is established.

At step 212, the mitigation analysis and output generation platform 103 may receive the client identification verification information sent at step 211. In one or more instances, the mitigation analysis and output generation platform 103 may receive the client identification verification information, via the communication interface 113, while the fourth wireless data connection is established.

At step 213, the mitigation analysis and output generation platform 103 may analyze the onboarding identification information received, at step 207, from the client device 102 and/or the sensor device 105, by comparing it to the client identification verification information received at step 212. For example, the mitigation analysis and output generation platform 103 may determine that a received fingerprint does not match a known fingerprint corresponding to the client. In another example, mitigation analysis and output generation platform 103 may determine that GPS data indicates that the client device 102 is located in a country different from the client's home country. In yet another example, the mitigation analysis and output generation platform 103 may determine that a different client conducted an onboarding process on the client device 102 within the last week. In yet another example, the mitigation analysis and output generation platform 103 may determine that identification information for the client is found on an inter-insurer database or clearinghouse containing the identifications of known fraudsters. In yet another example, the mitigation analysis and output generation platform 103 may determine that the user-provided information is not correlated with information found in a third-party database. In yet another example, the mitigation analysis and output generation platform 103 may determine that an amount of time elapsed since initiation of the onboarding process is significantly more than an anticipated amount of time spent to conduct the onboarding process. In one or more instances, the amount of time may be less than a predetermined contestability period. In one or more instances where the onboarding identification information corresponds to a photograph of the client, the mitigation analysis and output generation platform 103 may periodically receive updated photographs throughout the onboarding process, and may compare them to previously received photographs.

In one or more instances where the onboarding identification information corresponds to social media data, the mitigation analysis and output generation platform 103 may generate a facial recognition score for the client based on stored images of the client from the client verification database 106. In these instances, the mitigation analysis and output generation platform 103 may compare the generated facial recognition score to a facial recognition score of a photograph received as an onboarding identification input.

In one or more instances, where the onboarding identification information corresponds to a cell phone carrier or an individual to whom the client device 102 is registered, the mitigation analysis and output generation platform 103 may determine that the onboarding process is being conducted on a phone serviced by a different cell phone carrier from the one that the client uses. In yet another instance, the mitigation analysis and output generation platform 103 may determine that onboarding for the client is being conducted on a device that may belong to another individual.

With regard to fitness/activity data, in one or more instances, the mitigation analysis and output generation platform 103 may receive heart rate data or motion patterns from the client verification database 106. In these instances, the mitigation analysis and output generation platform 103 may compare a pulse received as an onboarding identification input during an alleged run with heart rate data for the client during various activities. In doing so, the mitigation analysis and output generation platform 103 may determine that the pulse corresponds to a bike ride, rather than a run (e.g., the client tried to cheat a fitness identification test during onboarding by riding a bike to move faster rather than running). As another example, the mitigation analysis and output generation platform 103 may determine that the pulse corresponds to a period of minimal activity, but a movement pattern is detected. Accordingly, the mitigation analysis and output generation platform 103 may determine that the pulse is more consistent with the client driving a car rather than running (e.g., the client tried to cheat a fitness identification test during onboarding by slowly driving a car to move faster than the client is able to run because the client may be out of shape).

With regard to movement data, in one or more instances, the mitigation analysis and output generation platform 103 may receive GPS data as to where the client device 102 and/or sensor device 105 has been traveling. The mitigation analysis and output generation platform 103 may also receive data from the client verification database 106 corresponding to a time and route of the client's typical commute to work. In these instances, the mitigation analysis and output generation platform 103 may compare the GPS data to the known routes.

Many determinations such as these may be made by the mitigation analysis and output generation platform 103 by comparing onboarding identification information, received at the time of onboarding, to stored client identification verification information from the client verification database 106. By comparing the onboarding identification information to the stored client verification identification information, the mitigation analysis and output generation platform 103 may effectively compare the received onboarding identification inputs to expected onboarding identification inputs. In one or more instances, the mitigation analysis and output generation platform 103 may analyze the onboarding identification information using one or more machine learning algorithms and datasets.

Referring to FIG. 2C, at step 214, the mitigation analysis and output generation platform 103 may generate a mitigation output based on the analysis performed at step 213. In one or more instances, by generating the mitigation output, the mitigation analysis and output generation platform 103 may determine a identification fraud probability confidence score corresponding to a probability that fraud was committed by the individual conducting the onboarding process (e.g., the individual providing the onboarding identification inputs is not who they claim to be or the authenticity of user-provided information could not be verified). In one or more instances, the identification fraud probability confidence score may be a score on a scale of 0-100, with 100 being the most likely that fraud is being committed.

At step 215, the mitigation analysis and output generation platform 103 may send the mitigation output, including the identification fraud probability confidence score, to the onboarding and policy management platform 104. In one or more instances, the mitigation analysis and output generation platform 103 may send the mitigation output, including the identification fraud probability confidence score, via the communication interface 113 and while the third wireless data connection is established.

At step 216, the onboarding and policy management platform 104 may receive the mitigation output and the identification fraud probability confidence score sent at step 215. In one or more instances, the onboarding and policy management platform 104 may receive the mitigation output and the identification fraud probability confidence score via the communication interface 116 and while the third wireless data connection is still established.

At step 217, the onboarding and policy management platform 104 may compare the identification fraud probability confidence score received at step 216 to one or more predetermined mitigation thresholds. In one or more instances, the onboarding and policy management platform 104 may determine the one or more predetermined mitigation thresholds based on a type of product corresponding to the onboarding process being conducted. For example, a life insurance policy may have lower predetermined mitigation thresholds than a car insurance policy (e.g., the identification verification process may be more stringent when purchasing a life insurance policy, than when purchasing a car insurance policy. As a result, it may be easier for a customer to exceed the thresholds when purchasing a life insurance policy, than when purchasing a car insurance policy, due to stricter identification requirements which must be met because the life insurance policy may be a more expensive policy than the car insurance policy, carry greater risks for the insurer or insured, or the like). For example, in some instances, the onboarding and policy management platform 104 may determine a first predetermined threshold, a second predetermined threshold, and a third predetermined threshold. For example, if the identification fraud probability confidence score is a score which ranges from 0-100 and the type of product that the client wishes to purchase is a life insurance policy, the first predetermined threshold may be 0, the second predetermined threshold may be 10, and the third predetermine threshold may be 30. As another example, if the identification fraud probability confidence score is a score which ranges from 0-100 and the type of product that the client wishes to purchase is a car insurance policy, the first predetermined threshold may be 0, the second predetermined threshold may be 20, and the third predetermine threshold may be 50. In some instances, the predetermined mitigation thresholds may depend on the complexity of the product being purchased. In other instances, the predetermined mitigation thresholds may not depend on the type or the complexity of the product, i.e., the thresholds may be the same for each product.

In comparing the identification fraud probability confidence score to the one or more predetermined mitigation thresholds, such as the first, second, and third predetermined thresholds, the onboarding and policy management platform 104 may determine if the identification fraud probability confidence score meets or is below the first predetermined threshold. If the identification fraud probability confidence score meets or is below the first predetermined threshold, the onboarding and policy management platform 104 may determine that no fraud was detected with respect to the client's onboarding identification inputs. For example, the first predetermined threshold may be 0. If the identification fraud probability confidence score is also 0 (e.g., meets or is below this first predetermined threshold), the onboarding and policy management platform 104 may determine that the client's onboarding identification inputs were trustworthy and not fraudulent. In this case, the onboarding and policy management platform 104 may allow the client to continue with the onboarding process. For example, the onboarding and policy management platform 104 may proceed to step 225 to begin collecting additional information from the client (e.g., health, fitness/activity, location, and other information, etc.) for determining whether the client is eligible to purchase the requested product.

If the onboarding and policy management platform 104 determines that the identification fraud probability confidence score exceeds the first predetermined threshold, the onboarding and policy management platform 104 may determine if the identification fraud probability confidence score meets or is below the second predetermined threshold that is greater than the first predetermined threshold. If the identification fraud probability confidence score exceeds the first predetermined threshold and meets or is below the second predetermined threshold, the onboarding and policy management platform 104 may determine that some small degree of fraud may be possible, though unlikely, with respect to the client's onboarding identification inputs. For example, the probability of fraud may be sufficiently small that it may be attributed to an anomaly in the analysis of the onboarding identification inputs or due to human error made by the client in providing the onboarding identification inputs. For example, the second predetermined threshold may be 10. If the identification fraud probability confidence score exceeds the first predetermined threshold of 0 and meets or is below the second predetermined threshold of 10, the onboarding and policy management platform 104 may determine that fraud may be possible, though unlikely, with respect to the client's onboarding identification inputs, and more likely due to human error or an anomaly in the analysis of the onboarding identification inputs. In this case, the onboarding and policy management platform 104 may allow the client to continue with the onboarding process. For example, the onboarding and policy management platform 104 may proceed to step 225 to begin collecting additional information from the client (e.g., health, fitness/activity, location, and other information, etc.) for determining whether the client is eligible to purchase the requested product.

If the onboarding and policy management platform 104 determines that the identification fraud probability confidence score exceeds the second predetermined threshold, the onboarding and policy management platform 104 may determine if the identification fraud probability confidence score meets or is below the third predetermined threshold that is greater than the first predetermined threshold and the second predetermined threshold. If the identification fraud probability confidence score exceeds the second predetermined threshold and meets or is below the third predetermined threshold, the onboarding and policy management platform 104 may determine that fraud may be likely with respect to the client's onboarding identification inputs. For example, the third predetermined threshold may be 30. If the identification fraud probability confidence score exceeds the second predetermined threshold of 10 and meets or is below the third predetermined threshold of 30, the onboarding and policy management platform 104 may determine that fraud may be likely with respect to the client's onboarding identification inputs. In this case, the onboarding and policy management platform 104 may not allow the client to continue with the onboarding process and, instead, may require that the client undergo traditional underwriting in order to determine eligibility for the requested product. The onboarding and policy management platform 104 may proceed to step 218 to notify the client management platform 107 that fraud was detected and that the client will require traditional underwriting in order to determine eligibility for the requested product.

If the onboarding and policy management platform 104 determines that the identification fraud probability confidence score exceeds the third predetermined threshold, the onboarding and policy management platform 104 may determine that fraud is more likely than not with respect to the client's onboarding identification inputs. For example, if the identification fraud probability confidence score exceeds the third predetermined threshold of 30, the onboarding and policy management platform 104 may determine that fraud is more likely than not with respect to the client's onboarding identification inputs. In this case, the onboarding and policy management platform 104 may reject the client's request for the product. The onboarding and policy management platform 104 may proceed to step 218 to notify the client management platform 107 that fraud was detected and that the client's request for the product is rejected.

At step 218, the onboarding and policy management platform 104 may establish a connection with the client management platform 107. In one or more instances, the onboarding and policy management platform 104 may establish a fifth wireless data connection with the client management platform 107 to link the onboarding and policy management platform 104 with the client management platform 107.

Referring to FIG. 2D, at step 219, the onboarding and policy management platform 104 may generate and send an indication to the client management platform 107 that fraud was detected with respect to the onboarding identification inputs provided by the client during the onboarding process and that either the client will require undergoing traditional underwriting in order to determine eligibility for the requested product as a result of the fraud determination or the client is ineligible for the requested product as a result of the fraud determination. In one or more instances, the onboarding policy management platform 104 may also generate one or more commands directing the client management platform 107 to generate and display a mitigation notification based on the indication of the fraud determination. In one or more instances, the onboarding and policy management platform 104 may send, via the communication interface 116 and while the fifth wireless data connection is established, the indication that fraud was detected and the one or more commands directing the client management platform 107 to generate and display the mitigation notification.

At step 220, the client management platform 107 may receive the indication of the fraud determination and the one or more commands directing the client management platform 107 to generate and display the mitigation notification sent at step 219. In one or more instances, the client management platform 107 may receive, via the communication interface 116 and while the fifth wireless data connection is established, the indication of the fraud determination and the one or more commands directing the client management platform 107 to generate and display the mitigation notification.

At step 221, the client management platform 107 may display the mitigation notification generated at step 220. In one or more instances, in displaying the mitigation notification, the client management platform 107 may display a graphical user interface similar to graphical user interface 605 or graphical user interface 610, which are shown in FIGS. 6A and 6B. For example, the client management platform 107 may display an alert to an employee or an agent associated with an institution, such as an insurance company, that the client failed the onboarding verification test so that the institution may take appropriate action regarding the fraud detection.

If at step 217, the onboarding and policy management platform 104 determined that that fraud is likely with respect to the client's onboarding identification inputs (e.g., if the identification fraud probability confidence score exceeds the second predetermined threshold and/or the third predetermined threshold), then step 222 may be performed.

At step 222, the onboarding and policy management platform 104 may generate and send, to the client device 102 and/or the sensor device 105, an indication of the eligibility determination. In some instances, the indication of the eligibility determination may indicate that an in-person interview or some other traditional method of underwriting will be necessary to determine the client's eligibility for the product (e.g., when the second predetermined threshold is exceeded but the third predetermined threshold is not exceeded). In some instances, the indication of the eligibility determination may indicate that the client is ineligible for the product (e.g., when the third predetermined threshold is exceeded). In one or more instances, the onboarding policy management platform 104 may also generate one or more commands directing the client device 102 and/or sensor device 105 to generate and display an eligibility notification based on the indication of the eligibility determination. In one or more instances, the onboarding and policy management platform 104 may send, via the communication interface 116 and while the first and second wireless data connections are established, the one or more commands directing the client device 102 and/or the sensor device 105 to generate and display the eligibility notification. Step 222 may be performed before, after, or concurrently with step 219. That is, the onboarding and policy management platform 104 may send the indication of the eligibility determination to the client device 102 and/or the sensor device 105 before, after, or at the same time that the indication of the fraud determination is sent to the client management platform 107.

At step 223, the client device 102 and/or the sensor device 105 may receive the indication of the eligibility determination and the one or more commands directing the client device 102 and/or the sensor device 105 to generate and display the eligibility notification sent at step 222. In one or more instances, the client device 102 and/or the sensor device 105 may receive, via the communication interface 116 and while the first and second wireless data connections are established, the indication of the eligibility determination and the one or more commands directing the client device 102 and/or the sensor device 105 to generate and display the eligibility notification.

At step 224, the client device 102 and/or the sensor device 105 may display the eligibility notification generated at step 222. In one or more instances, in displaying the eligibility notification, the client device 102 and/or the sensor device 105 may display a graphical user interface similar to graphical user interface 705 or graphical user interface 710, shown in FIGS. 7A and 7B. For example, in some instances, as shown in FIG. 7A, the client device 102 and/or the sensor device 105 may display a notification indicating that an in-person interview will be necessary to determine eligibility, and in some instances may prompt the client to input scheduling information. Additionally or alternatively, the client device 102 and/or sensor device 105 may use the video call connection established with the client management platform 107 in step 201 to schedule or conduct the interview. In other instances, as shown in FIG. 7B, the client device 102 and/or the sensor device 105 may display a notification indicating that the client is not eligible for the requested product.

If at step 217, the onboarding and policy management platform 104 determined that that fraud was not detected or is unlikely with respect to the client's onboarding identification inputs (e.g., if the identification fraud probability confidence score is below the first predetermined threshold or the second predetermined threshold), then step 225 may be performed.

At step 225, the onboarding and policy management platform 104 may initiate the collection of additional information from the client for determining whether the client is eligible to purchase the requested product. The additional information may be onboarding personal information, such as health, fitness/activity, location, and other information. For instance, at step 225, the onboarding and policy management platform 104 may generate and send one or more commands directing the client device 102 and/or the sensor device 105 to generate and display a client onboarding interface for initiating the collection of the onboarding personal information. In one or more instances, the onboarding and policy management platform 104 may send, via the communication interface 116 and while the first and second wireless data connections are established, the one or more commands directing the client device 102 and/or the sensor device 105 to generate and display the client onboarding interface.

At step 226, the client device 102 and/or the sensor device 105 may receive the one or more commands directing the client device 102 and/or the sensor device 105 to generate and display the client onboarding interface for initiating the collection of the onboarding personal information. In one or more instances, the client device 102 and/or the sensor device 105 may receive, via the communication interface 116 and while the first and second wireless data connections are established, the one or more commands directing the client device 102 and/or the sensor device 105 to generate and display the client onboarding interface initiating the collection of the onboarding personal information.

At step 227, client device 102 and/or the sensor device 105 may generate and display the client onboarding interface for initiating collection of the onboarding personal information, e.g., the client's health, fitness/activity, location, and other information. In displaying the client onboarding interface, the client device 102 and/or sensor device 105 may generate and display a graphical user interface similar to graphical user interface 515, which is shown in FIG. 5C. In one or more instances, the client device 102 and/or sensor device 105 may prompt the client for permission to collect, access, analyze, and/or process the client's personal information, such as health, fitness/activity, location, and/or other information related to the client. In some instances, the client device 102 and/or the sensor device 105 may prompt the client for permission to collect, access, analyze, and/or process specific types of personal information stored on the client device 102 and/or the sensor device 105 or with a third-party database. The specific types may relate to health records, lab results, medical test results, clinical vital statistics, pulse, blood pressure, step count data, stairs climbed data, active minutes, prescription (Rx) data, sleep data, motor vehicle records (MVRs), credit reports, medical information bureau (MIB) records, social media data, etc. In some instances, the user may provide permission for collecting, accessing, analyzing, and/or processing one or more of the specific types of personal information stored on the client device 102 and/or the sensor device 105 or with a third-party database.

At step 228, the client device 102 and/or the sensor device 105 may send, to the onboarding and policy management platform 104, an indication of the specific types of personal information that the client provided permission to collect, access, analyze and/or process.

At step 229, the onboarding and policy management platform 104 may receive, from the client device 102 and/or the sensor device 105, the indication of the specific types of personal information that the client provided permission to collect, access, analyze and/or process.

At step 230, the onboarding and policy management platform 104 may send, to the client device 102, the sensor device 105, and/or to one or more external sources (not shown in FIG. 2E), one or more commands to retrieve the onboarding personal information as specified by the client provided permission.

For instance, the onboarding and policy management platform 104 may send, to the client device 102 and/or the sensor device 105, one or more commands to retrieve health and fitness/activity related data associated with the client. For example, the onboarding and policy management platform 104 may send, to the client device 102 and/or the sensor device 105, one or more commands to retrieve step count data, stairs climbed, active minutes, sleep data, heart rate data, blood pressure data, electrocardiogram (ECG or EKG) data, etc. for a predetermined time period. The predetermined time period may be hours, days, weeks, years, etc. In some instances, the onboarding and policy management platform 104 may send one or more commands to retrieve health and fitness/activity related data from an application, operating on the client device 102 and/or the sensor device 105, which stores health records and/or fitness/activity data.

In some instances, the onboarding and policy management platform 104 may send, to the client device 102 and/or the sensor device 105, one or more commands to retrieve location data or movement data, such as GPS data, indicating one or more locations or movement patterns of the client device 102 and/or the sensor device 105 over a predetermined time period.

In some instances, the onboarding and policy management platform 104 may send, to the client device 102 and/or the sensor device 105, one or more commands to retrieve data related to the client's purchase history for a predetermined time period. Such purchase history may be determined from purchases made using the client device 102 and/or the sensor device 105, via an electronic payment application, such as one or more mobile device payment applications. Such purchase history may additionally be determined from receipts stored on the client device 102 and/or the sensor device 105.

In some instances, the onboarding and policy management platform 104 may send one or more commands to a system associated with MVRs to retrieve data associated with the client's MVRs covering a predetermined time period.

In some instances, the onboarding and policy management platform 104 may send one or more commands to a system associated with MIB to retrieve data associated with the client's MIB records covering a predetermined time period.

In some instances, the onboarding and policy management platform 104 may send one or more commands to a system associated with a credit bureau to retrieve data associated with the client's credit history records covering a predetermined time period.

In some instances, the onboarding and policy management platform 104 may send one or more commands to a medical billing system to receiving the client's medical billing records covering a predetermined period of time.

In some instances, the onboarding and policy management platform 104 may send one or more commands to a system associated with a social networking service with which the client is associated to retrieve social networking data associated with the client and covering a predetermined time period. The social networking data to be retrieved may be data which tends to indicate the client's habits, behaviors, lifestyle choices, and/or health/wellness/fitness status. The data may include social networking profile information; friends or connections; groups, organizations, causes, etc. with which the client is associated; messages, chats, posts or comments made by or about the client indicating a behavior of the client; images or video posted by or including the client exhibiting certain behaviors of the client, etc. For example, images showing or posts commenting on a user smoking or skydiving may tend to reflect risky behavior on the part of the user, while images showing or posts commenting on the user exercising or engaging in healthy eating may tend to reflect positive behavior on the part of the user.

In some instances, the predetermined time period for which the various types of data may be retrieved may be different for each type of data. For example, the onboarding and policy management platform 104 may send one or more commands to retrieve three years of records related to the client's credit card history, but may send one or more commands to retrieve only one year of purchase history records related to the client. In some instances, the predetermined time period for which the various types of data may be retrieved may be the same for each type of data. For example, the onboarding and policy management platform 104 may send one or more commands to retrieve three years of records related to the client's credit card history and three years of purchase history records related to the client.

At step 231, the client device 102, the sensor device 105, and/or one or more external sources (not shown) may receive, from the onboarding and policy management platform 104, the one or more commands to retrieve the onboarding personal information.

At step 232, the client device 102, the sensor device 105, and or the one or more external sources (not shown) may retrieve the onboarding personal information. The retrieved onboarding personal information (e.g., the health data, fitness/activity data, location data, purchase history data, credit history data, MVRs data, MIB data, medical billing records data, health records data, Rx data, social networking data, etc.), may be sent to the onboarding and policy management platform 104 for aggregation and analysis. Alternatively, for privacy and or other reasons, the onboarding and policy management platform 104 may instruct the client device 102 and/or the sensor device 105 to aggregate and analyze the retrieved onboarding personal information itself.

At step 233, the onboarding and policy management platform 104 may receive the onboarding personal information sent from the client device 102, the sensor device 105, and or the one or more external sources (not shown).

At step 234, the onboarding and policy management platform 104 may generate and send one or more commands to the mitigation analysis and output generation platform 103 directing the mitigation analysis and output generation platform 103 to analyze the onboarding personal information. The onboarding and policy management platform 104 may send the onboarding personal information together with the one or more commands directing the mitigation analysis and output generation platform 103 to analyze the onboarding personal information.

At step 235, the mitigation analysis and output generation platform 103 may receive the onboarding personal information and the one or more commands directing the mitigation analysis and output generation platform 103 to analyze the onboarding personal information. The one or more commands may include instructions to retrieve personal verification information for use in performing certain aspects of the analysis of the onboarding personal information.

At step 236, the mitigation analysis and output generation platform 103 may generate one or more commands directing the client verification database 106 to determine client personal or health verification information and may send the commands to the client verification database 106.

At step 237, the client verification database 106 may receive the one or more commands, that were sent at step 235, directing the client verification database 106 to determine the client personal or health verification information.

At step 238, the client verification database 106 may determine client personal or health verification information corresponding to the onboarding personal information retrieved at step 232. The client verification database 106 may maintain data that may be used as a reference point to verify the onboarding personal information received from the client device 102, the sensor device 105, and/or the one or more external sources. In one or more instances, the client verification database 106 may obtain the client personal or health verification information via user input from the clients themselves. Additionally or alternatively, the client verification database 106 may access one or more internal or external databases to obtain the client personal or health verification information.

Once the client verification database 106 determines the client personal or health verification information corresponding to the alleged client, the client verification database 106 may send the client personal or health verification information to the mitigation analysis and output generation platform 103.

At step 239, the mitigation analysis and output generation platform 103 may receive the client personal or health verification information sent at step 237.

At step 240, the mitigation analysis and output generation platform 103 may analyze the onboarding personal information by performing cross-verification of the onboarding personal information. The mitigation analysis and output generation platform 103 may additionally use the personal verification information received at step 239 in performing the analysis. The analysis may be performed to detect any abnormal or irregular patterns in the onboarding personal information which may signal the possibility of fraud. Such abnormal or irregular patterns may occur when, for example, a client uploads someone else's data, does not disclose patient accounts for health records from health providers that have a history of the individual's recent medical conditions (such as a diagnosis of chronic illness), doesn't disclose all relevant data, or attempts to alter or manipulate the data, such as by manipulating a clock in one or more devices used to capture the data (e.g., to submit duplicate steps data from different devices) or by using a fitness application's legitimate feature to manually enter data (e.g., step count) to enter inaccurate data. To detect these and other potential abnormalities in the onboarding personal information, the mitigation analysis and output generation platform 103 may perform various analysis functions to cross-check the data which was received from the various sources (e.g., the health data, fitness/activity data, location data, purchase history data, credit history data, MVRs data, health records, MIB data, Rx data, medical billing records data, social networking data, etc.).

In performing each of the various analysis functions, the mitigation and output generation platform 103 may determine a personal information fraud probability confidence sub-score corresponding to a probability of fraud with respect to data being analyzed. As an example, the personal information fraud probability confidence sub-score may be a score on a scale of 0-10, where 0 indicates that no fraud was detected and 10 indicates that fraud is more likely than not. The personal information fraud probability confidence sub-score may not be limited to a scale of 0-10, and may instead be, for example, on a scale of 1-100, A-F, or the like. After determining a personal information fraud probability confidence sub-score for each of the various analysis functions, the mitigation and output generation platform 103 may use the sub-scores to determine a personal information fraud probability confidence overall score. The personal information fraud probability confidence overall score may reflect an overall determination regarding the probability that the client provided fraudulent data during the onboarding process. The sub-scores may be summed, averaged, or weighted and then summed to calculate the overall score.

In some instances, the mitigation analysis and output generation platform 103 may identify, in the onboarding personal information, a device identifier identifying a device used to capture the corresponding data. The unique identifier may be a telephone number, an International Mobile Subscriber Identity (IMSI) value, an International Mobile Equipment Identity (IMEI) value, a Temporary Mobile Subscriber Identity IMSI value, an email address, etc. For example, the telephone number of the device used to capture step count data, vital signs data, or location data, etc. may be identified in the onboarding personal information. The mitigation analysis and output generation platform 103 may compare device identifiers associated with the different types of data to confirm that the data was captured by the same device. In some instances, such as when the data is not captured by the user's device, but is instead retrieved from an external data source, the onboarding personal information may identify a unique identifier, such as an email, an account number, or other identifier, associated with the corresponding data. For example, MVR data may be associated with a driver's license number, and social networking data may be associated with an email address. In some instances, the mitigation and output generation platform 103 may use the personal verification information to confirm that different types of identifiers are associated with the same client. For example, the mitigation and output generation platform 103 may use the personal verification information to confirm that a device identifier used to capture certain data, an email address associated with other data, and a driver's license number associated with yet other data are all associated with the same client. Based on this analysis, the mitigation and output generation platform 103 may determine a first personal information fraud probability confidence sub-score corresponding to a probability of fraud with respect to ownership of the data included in the onboarding personal information. For example, when the mitigation and output generation platform 103 detects an inconsistency in the ownership of the data included in the onboarding personal information, the mitigation analysis and output generation platform 103 may determine the first personal information fraud probability confidence sub-score to be a value greater than 0.

In some instances, the mitigation analysis and output generation platform 103 may determine whether the onboarding personal information for a client is the same as or has a threshold level of similarity with onboarding personal information for other insurance applications the client has applied for within a predetermined period of time. The mitigation analysis and output generation platform 103 may compare onboarding personal information (and the device identifiers and other unique identifiers associated with the data) between different insurance applications made by the client to ensure that the client is providing the same or similar data, within a threshold amount, for all of the applications made by the client within a predetermined period of time. Based on this analysis, the mitigation and output generation platform 103 may determine a second personal information fraud probability confidence sub-score corresponding to a probability of fraud with respect to the onboarding personal information between different insurance applications. For example, when the mitigation and output generation platform 103 detects an inconsistency between the onboarding personal information of different insurance applications made by the client, or client data obtained from various data sources, the mitigation analysis and output generation platform 103 may determine the second personal information fraud probability confidence sub-score to be a value greater than 0.

In some instances, the mitigation analysis and output generation platform 103 may identify, from the onboarding personal information, data acquired from a fitness account associated with a wearable fitness device. The mitigation analysis and output generation platform 103 may further identify, from the onboarding personal information, data acquired from a social networking account. The fitness account data and the social networking account data may both include friends lists corresponding to each account, respectively. The mitigation analysis and output generation platform 103 may compare the friends lists from both account to confirm a threshold percentage of matching friends between the two accounts. Based on this analysis, the mitigation and output generation platform 103 may determine a third personal information fraud probability confidence sub-score corresponding to a probability of fraud with respect to the client's various friends lists. For example, when the mitigation and output generation platform 103 detects an inconsistency between the friends lists of various of the client's accounts, the mitigation analysis and output generation platform 103 may determine the third personal information fraud probability confidence sub-score to be a value greater than 0.

In some instances, the mitigation analysis and output generation platform 103 may identify, from the onboarding personal information, fitness/activity data acquired from more than one device or from more than one application executing on a single device. For example, the client may have captured fitness/activity data from both a wearable device and also a smartphone. Alternatively or additionally, the client may have captured fitness/activity data using two different applications executing on the same device. The mitigation analysis and output generation platform 103 may compare the fitness/activity data, e.g., step count, location data, sleep patterns, and/or time, from the various devices and/or applications. If the time data is substantially the same, but the step count, location data associated with the steps, and/or sleep patterns differ by more than a threshold amount, the mitigation analysis and output generation platform 103 may determine that fraud may be likely with respect to the fitness/activity data. If the step count, location data, and/or sleep patterns do not differ by more than a threshold amount, the mitigation analysis and output generation platform 103 may maintain the fitness/activity data from a selected preferred source of the various devices and discard the fitness/activity data from the other sources, so as to avoid duplicate counting of the fitness/activity data, such as step count data. Additionally, if the time data is different, but the step count and the location data match within a threshold amount, the mitigation analysis and output generation platform 103 may determine that fraud may be likely with respect to the fitness/activity data. Based on this analysis, the mitigation and output generation platform 103 may determine a fourth personal information fraud probability confidence sub-score corresponding to a probability of fraud with respect to the fitness/activity data. For example, when the mitigation and output generation platform 103 detects an inconsistency between the fitness/activity data captured by different devices, the mitigation analysis and output generation platform 103 may determine the fourth personal information fraud probability confidence sub-score to be a value greater than 0.

In some instances, the mitigation analysis and output generation platform 103 may identify, from the onboarding personal information, fitness/activity data acquired from more than one device. The mitigation analysis and output generation platform 103 may compare the step count data from one device with the sleep data from another device to identify inconsistencies. For example, if the step count data captured in a first device indicates a number of steps above a threshold amount at a time where the sleep data on a second device indicates that the client was sleeping, the mitigation analysis and output generation platform 103 may determine that fraud may be likely with respect to the fitness/activity data. Based on this analysis, the mitigation and output generation platform 103 may determine a fifth personal information fraud probability confidence sub-score corresponding to a probability of fraud with respect to the fitness/activity data. For example, when the mitigation and output generation platform 103 detects an inconsistency between the step count data and sleep data captured by different devices, the mitigation analysis and output generation platform 103 may determine the fifth personal information fraud probability confidence sub-score to be a value greater than 0.

In some instances, the mitigation analysis and output generation platform 103 may identify, from the onboarding personal information, step data and accelerometer data at the time the step data was captured. The mitigation analysis and output generation platform 103 may use the accelerometer data to determine whether movement or step patterns in the step data reflect a human pattern of movement, or whether the step patterns are too mechanical (e.g., lacking in variation), such as reflecting movement patterns from a machine or robot, or perhaps movement patterns of an animal, such as a dog or a cat. For example, the mitigation analysis and output generation platform 103 may generate and store average movement or step pattern data based on analyzing the movement and step pattern data of a plurality of users. The mitigation analysis and output generation platform 103 may compare the movement/step pattern data received from the onboarding personal information with the stored average step pattern data in order to determine whether the step pattern data received from the onboarding personal information deviates from the average movement/step pattern data by more than a threshold amount. If the step pattern data received from the onboarding personal information deviates from the average movement/step pattern data by more than the threshold amount, the step pattern may be determined to be abnormal, and the mitigation analysis and output generation platform 103 may determine that fraud may be likely with respect to the step data. Based on this analysis, the mitigation and output generation platform 103 may determine a sixth personal information fraud probability confidence sub-score corresponding to a probability of fraud with respect to the step data. For example, when the mitigation and output generation platform 103 detects an abnormality with the step data, the mitigation analysis and output generation platform 103 may determine the sixth personal information fraud probability confidence sub-score to be a value greater than 0.

In some instances, the mitigation analysis and output generation platform 103 may identify, from the onboarding personal information, step data and movement/location data associated with the step data. The step data may indicate whether step count data was captured automatically or whether a user manually entered the step count data via an application. If the step count data was entered manually and the associated location data indicates that the client was moving at a speed greater than a predetermined threshold, e.g., faster than a human is able to walk or run, when the step count data was captured, and instead was moving at vehicular speeds, for example, the mitigation analysis and output generation platform 103 may determine that fraud may be likely with respect to the step data. Based on this analysis, the mitigation and output generation platform 103 may determine a seventh personal information fraud probability confidence sub-score corresponding to a probability of fraud with respect to the step data. For example, when the mitigation and output generation platform 103 detects an abnormality with the step data, the mitigation analysis and output generation platform 103 may determine the seventh personal information fraud probability confidence sub-score to be a value greater than 0.

In some instances, the mitigation analysis and output generation platform 103 may identify, from the onboarding personal information, health records data. The health records data may include indications of when various records within the health records data were last updated. Records updated within a threshold period of time from submission of the health records data via the onboarding process or different records with similar update patterns may be determined to be suspicious, and the mitigation analysis and output generation platform 103 may determine that fraud may be likely with respect to the health records data. Based on this analysis, the mitigation and output generation platform 103 may determine an eighth personal information fraud probability confidence sub-score corresponding to a probability of fraud with respect to the health records data. For example, when the mitigation and output generation platform 103 detects an abnormality with the health records data, the mitigation analysis and output generation platform 103 may determine the eighth personal information fraud probability confidence sub-score to be a value greater than 0.

In some instances, the mitigation analysis and output generation platform 103 may identify, from the onboarding personal information, Rx data collected from various sources. For example, the Rx data may be included in health records data or may be collected from an Rx database which maintains prescription history data from various pharmacies. When more than a threshold number of inconsistencies between the Rx data collected from the various sources are identified, the mitigation analysis and output generation platform 103 may determine that fraud may be likely with respect to the Rx data. For example, if the Rx data included in the health records data identifies 2 prescriptions associated with the individual, and the Rx data included in the Rx database identifies 25 prescriptions associated with the individual, the mitigation analysis and output generation platform 103 may determine that fraud may be likely with respect to the Rx data. Based on this analysis, the mitigation and output generation platform 103 may determine a ninth personal information fraud probability confidence sub-score corresponding to a probability of fraud with respect to the Rx data. For example, when the mitigation and output generation platform 103 detects inconsistencies in Rx data between various sources, the mitigation analysis and output generation platform 103 may determine the ninth personal information fraud probability confidence sub-score to be a value greater than 0.

In some instances, the mitigation analysis and output generation platform 103 may identify, from the onboarding personal information, medical condition data and Rx data collected from various sources. The Rx data may be included in health records data or may be collected from an Rx database which maintains prescription history data from various pharmacies. The medical condition may be self-identified by the client, may be known from a previous application from the client, may be included in the client's health records data, may be inferred from social media, etc. The mitigation analysis and output generation platform 103 may compare the Rx data to the medical conditions of the client. For example, if the client is determined to have a medical condition such as diabetes or asthma and no corresponding prescription, such as insulin or an inhaler, to treat the condition is identified in the Rx data, or prescriptions related to chronic illness in Rx data are not represented in the health records data, or if the medical condition and the Rx data are inconsistent or incompatible, the mitigation analysis and output generation platform 103 may determine that fraud may be likely with respect to the Rx data and/or the medical condition data. Based on this analysis, the mitigation and output generation platform 103 may determine a tenth personal information fraud probability confidence sub-score corresponding to a probability of fraud with respect to the Rx and/or medical conditions data. For example, when the mitigation and output generation platform 103 detects inconsistencies between Rx data and medical conditions data, the mitigation analysis and output generation platform 103 may determine the tenth personal information fraud probability confidence sub-score to be a value greater than 0.

In some instances, the mitigation analysis and output generation platform 103 may identify, from the onboarding personal information, purchase history data. Such purchase history may be determined from purchases made using the client device 102 and/or the sensor device 105, via an electronic payment application. Such purchase history may additionally be determined from receipts stored on the client device 102 and/or the sensor device 105. The mitigation analysis and output generation platform 103 may identify from the purchase history data point-of-sale prescription related purchases. The purchase history data may indicate a date, time and location of the point-of-sale prescription purchases. The mitigation analysis and output generation platform 103 may compare the location data associated with the point-of-sale prescription purchases to location data captured by the client device 102 and/or the sensor device 105 at the date and time indicated by the purchase history data, to identify any inconsistencies. The mitigation analysis and output generation platform 103 may additionally compare prescriptions identified from the point-of-sale prescription purchases with Rx data included in the onboarding personal information. The Rx data may be included in health records data or may be collected from an Rx database which maintains prescription history data from various pharmacies. The mitigation analysis and output generation platform 103 may determine whether there are prescriptions identified in the Rx data corresponding to the prescriptions identified in the point-of-sale prescription purchases. If inconsistencies are identified with the point-of-sale prescription purchases and the corresponding location data from the client device 102 and/or the sensor device 105 or with the Rx data, the mitigation analysis and output generation platform 103 may determine that fraud may be likely with respect to the purchase history and/or Rx data. Based on this analysis, the mitigation and output generation platform 103 may determine an eleventh personal information fraud probability confidence sub-score corresponding to a probability of fraud with respect to the purchase history and/or Rx data. For example, when the mitigation and output generation platform 103 detects inconsistencies between the purchase history data and/or the Rx data, the mitigation analysis and output generation platform 103 may determine the eleventh personal information fraud probability confidence sub-score to be a value greater than 0.

In some instances, the mitigation analysis and output generation platform 103 may identify, from the onboarding personal information, ECG data collected from various sources. The ECG data may be included in health records data or may be collected from a device, such as a smart watch. The mitigation analysis and output generation platform 103 may compare the ECG data from the different sources to detect any differences above a threshold amount in the corresponding ECG patterns. The mitigation analysis and output generation platform 103 may additionally compare ECG data captured from a single source over a period of time to detect any differences above a threshold amount in the ECG patterns over time. The mitigation analysis and output generation platform 103 may also identify medical conditions of the client. The medical condition may be self-identified by the client, may be known from a previous application from the client, may be included in the client's health records data, may be inferred from social media, etc. The mitigation analysis and output generation platform 103 may compare the ECG data to the medical conditions of the client to identify any inconsistencies between the data. When abnormal ECG patterns over time or between sources are identified or when inconsistencies between ECG data and medical conditions data is identified, the mitigation analysis and output generation platform 103 may determine that fraud may be likely with respect to the ECG data and/or the medical condition data. Based on this analysis, the mitigation and output generation platform 103 may determine a twelfth personal information fraud probability confidence sub-score corresponding to a probability of fraud with respect to the ECG data and/or medical conditions data. For example, when the mitigation and output generation platform 103 detects inconsistencies with the ECG data and/or the medical conditions data, the mitigation analysis and output generation platform 103 may determine the twelfth personal information fraud probability confidence sub-score to be a value greater than 0.

In some instances, the mitigation analysis and output generation platform 103 may identify, from the onboarding personal information, pulse and/or motion pattern data for various activities. The mitigation analysis and output generation platform 103 may also receive pulse data or motion patterns for the client from the client verification database 106. The mitigation analysis and output generation platform 103 may compare the pulse and/or motion pattern data for a particular activity in the onboarding personal information with pulse and/or motion pattern data stored in the client verification database 106 for the same activity. In doing so, the mitigation analysis and output generation platform 103 may determine that the pulse and/or motion pattern data for the particular activity in the onboarding personal information are inconsistent with the data for the same activity in the client verification database 106. For example, if the pulse and/or motion pattern data identified as corresponding to a run in the onboarding personal information instead is similar to the client's pulse and/or motion pattern data for a bike ride in the client verification database 106, the mitigation analysis and output generation platform 103 may determine that the pulse and/or motion pattern data in onboarding personal information is suspicious. As another example, the mitigation analysis and output generation platform 103 may determine that the pulse data in the onboarding personal information corresponds to a period of minimal activity, while movement pattern data is also detected in the onboarding personal information. Accordingly, the mitigation analysis and output generation platform 103 may determine that the pulse corresponds to driving a car rather than running. As another example, the onboarding personal information may include GPS data corresponding to where the client device 102 and/or sensor device 105 has traveled. The mitigation analysis and output generation platform 103 may also receive data from the client verification database 106 corresponding to a time and route of the client's typical commute to work. The mitigation analysis and output generation platform 103 may compare the GPS data to the known routes, to identify any inconsistencies. When inconsistencies are identified with respect to the pulse and/or movement pattern data, the mitigation analysis and output generation platform 103 may determine that fraud may be likely with respect to the pulse and/or movement pattern data. Based on this analysis, the mitigation and output generation platform 103 may determine a thirteenth personal information fraud probability confidence sub-score corresponding to a probability of fraud with respect to the pulse and/or movement pattern data. For example, when the mitigation and output generation platform 103 detects inconsistencies with pulse and/or movement pattern data, the mitigation analysis and output generation platform 103 may determine the thirteenth personal information fraud probability confidence sub-score to be a value greater than 0.

The mitigation analysis and output generation platform 103 may perform various other analysis functions with respect to the onboarding personal information to detect any inconsistencies or abnormal conditions with respect to the data. The mitigation analysis and output generation platform 103 may as a result determine one or more additional personal information fraud probability confidence sub-scores.

At step 241, the mitigation analysis and output generation platform 103 may generate a mitigation output based on the analysis performed at step 240. In one or more instances, by generating the mitigation output, the mitigation analysis and output generation platform 103 may determine the personal information fraud probability confidence overall score reflecting an overall determination regarding the probability that the client provided fraudulent data during the onboarding process. The mitigation analysis and output generation platform 103 may use the various personal information fraud probability confidence sub-scores to determine the personal information fraud probability confidence overall score. The overall score may be determined by summing, averaging, or weighting and then summing the sub-scores. For example, the sub-scores may be weighted such that when summed the overall score may fall on a scale of 0-100, with 100 being the most likely that fraud is being committed.

Referring to FIG. 2G, at step 242, the mitigation analysis and output generation platform 103 may send the mitigation output, including the personal information fraud probability confidence overall score, to the onboarding and policy management platform 104. In one or more instances, the mitigation analysis and output generation platform 103 may send the mitigation output, including the personal information fraud probability confidence overall score, via the communication interface 113 and while the third wireless data connection is established.

At step 243, the onboarding and policy management platform 104 may receive the mitigation output and the personal information fraud probability confidence overall score sent at step 242. In one or more instances, the onboarding and policy management platform 104 may receive the mitigation output and the personal information fraud probability confidence overall score via the communication interface 116 and while the third wireless data connection is still established.

At step 244, the onboarding and policy management platform 104 may compare the personal information fraud probability confidence overall score received at step 243 to one or more predetermined mitigation thresholds. The onboarding and policy management platform 104 may determine the one or more predetermined mitigation thresholds and compare the personal information fraud probability confidence overall score to the thresholds in a manner similar to that described in step 217. For example, the personal information fraud probability confidence overall score may be compared to a first, second, and third predetermined threshold.

If the onboarding and policy management platform 104 determines that the personal information fraud probability confidence overall score meets or is below the first predetermined threshold, the onboarding and policy management platform 104 may determine that no fraud was detected with respect to the client's onboarding personal information. In this case, the onboarding and policy management platform 104 may allow the client to finalize the onboarding process and purchase the requested product. For example, the onboarding and policy management platform 104 may proceed to step 251 to finalize the onboarding process.

If the onboarding and policy management platform 104 determines that the personal information fraud probability confidence overall score exceeds the first predetermined threshold and meets or is below the second predetermined threshold that is greater than the first predetermined threshold, the onboarding and policy management platform 104 may determine that some small degree of fraud may be possible, though unlikely, with respect to the client's onboarding personal information. For example, the probability of fraud may be sufficiently small that it may be attributed to an anomaly in the analysis of the onboarding personal information or due to human error in the collection of the data at the source. In this case, the onboarding and policy management platform 104 may allow the client to finalize the onboarding process and purchase the requested product. For example, the onboarding and policy management platform 104 may proceed to step 251 to finalize the onboarding process.

If the onboarding and policy management platform 104 determines that the personal information fraud probability confidence overall score exceeds the second predetermined threshold and meets or is below the third predetermined threshold that is greater than the first predetermined threshold and the second predetermined threshold, the onboarding and policy management platform 104 may determine that fraud may be likely with respect to the client's onboarding personal information. In this case, the onboarding and policy management platform 104 may not allow the client to purchase the requested product via the onboarding process and, instead, may require that the client undergo traditional underwriting in order to determine eligibility for the requested product. The onboarding and policy management platform 104 may proceed to step 245 to notify the client management platform 107 that fraud was detected and that the client will require traditional underwriting in order to determine eligibility for the requested product.

If the onboarding and policy management platform 104 determines that the personal information fraud probability confidence score exceeds the third predetermined threshold, the onboarding and policy management platform 104 may determine that fraud is more likely than not with respect to the client's onboarding personal information. In this case, the onboarding and policy management platform 104 may reject the client's request for the product. The onboarding and policy management platform 104 may proceed to step 245 to notify the client management platform 107 that fraud was detected and that the client's request for the product is rejected.

At step 245, the onboarding and policy management platform 104 may generate and send an indication to the client management platform 107 that fraud was detected with respect to the onboarding personal information and that either the client will require undergoing traditional underwriting in order to determine eligibility for the requested product as a result of the fraud determination, or the client is ineligible for the requested product as a result of the fraud determination. In one or more instances, the onboarding policy management platform 104 may also generate one or more commands directing the client management platform 107 to generate and display a mitigation notification based on the indication of the fraud determination. In one or more instances, the onboarding and policy management platform 104 may send, via the communication interface 116 and while the fifth wireless data connection is established, the indication that fraud was detected and the one or more commands directing the client management platform 107 to generate and display the mitigation notification.

At step 246, the client management platform 107 may receive the indication of the fraud determination and the one or more commands directing the client management platform 107 to generate and display the mitigation notification. In one or more instances, the client management platform 107 may receive, via the communication interface 116 and while the fifth wireless data connection is established, the indication of the fraud determination and the one or more commands directing the client management platform 107 to generate and display the mitigation notification.

At step 247, the client management platform 107 may display the mitigation notification. In one or more instances, in displaying the mitigation notification, the client management platform 107 may display a graphical user interface similar to graphical user interface 605 or graphical user interface 610, which are shown in FIGS. 6A and 6B. For example, the client management platform 107 may display an alert to an employee of an institution, such as an insurance company, that the client failed the onboarding process so that the institution may take appropriate action regarding the fraud detection.

If at step 244, the onboarding and policy management platform 104 determined that that fraud is likely with respect to the client's onboarding personal information (e.g., if the personal information fraud probability confidence overall score exceeds the second predetermined threshold and/or the third predetermined threshold), then step 248 may be performed.

At step 248, the onboarding and policy management platform 104 may generate and send, to the client device 102 and/or the sensor device 105, an indication of the eligibility determination. In some instances, the indication of the eligibility determination may indicate that an in-person interview or some other traditional method of underwriting will be necessary to determine the client's eligibility for the product (e.g., when the personal information fraud probability confidence overall score exceeds the second predetermined threshold but not the third predetermined threshold). In some instances, the indication of the eligibility determination may indicate that the client is ineligible for the product (e.g., when the personal information fraud probability confidence overall score exceeds the third predetermined threshold). In one or more instances, the onboarding policy management platform 104 may also generate one or more commands directing the client device 102 and/or sensor device 105 to generate and display an eligibility notification based on the indication of the eligibility determination. In one or more instances, the onboarding and policy management platform 104 may send, via the communication interface 116 and while the first and second wireless data connections are established, the one or more commands directing the client device 102 and/or the sensor device 105 to generate and display the eligibility notification. Step 248 may be performed before, after, or concurrently with step 245. That is, the onboarding and policy management platform 104 may send the indication of the eligibility determination to the client device 102 and/or the sensor device 105 before, after, or at the same time that the indication of the fraud determination is sent to the client management platform 107.

At step 249, the client device 102 and/or the sensor device 105 may receive the indication of the eligibility determination and the one or more commands directing the client device 102 and/or the sensor device 105 to generate and display the eligibility notification sent at step 248. In one or more instances, the client device 102 and/or the sensor device 105 may receive, via the communication interface 116 and while the first and second wireless data connections are established, the indication of the eligibility determination and the one or more commands directing the client device 102 and/or the sensor device 105 to generate and display the eligibility notification.

Referring to FIG. 2H, at step 250, the client device 102 and/or the sensor device 105 may display the eligibility notification. In one or more instances, in displaying the eligibility notification, the client device 102 and/or the sensor device 105 may display a graphical user interface similar to graphical user interface 705 or graphical user interface 710, shown in FIGS. 7A and 7B. For example, in some instances, as shown in FIG. 7A, the client device 102 and/or the sensor device 105 may display a notification indicating that an in-person interview will be necessary to determine eligibility, and in some instances may prompt the client to input scheduling information. Additionally or alternatively, the client device 102 and/or sensor device 102 may use the video call connection established with the client management platform 107 in step 201 to schedule or conduct the interview. In other instances, as shown in FIG. 7B, the client device 102 and/or the sensor device 105 may display a notification indicating that the client is not eligible for the requested product.

If at step 244, the onboarding and policy management platform 104 determined that that fraud was not detected or is unlikely with respect to the client's onboarding identification inputs (e.g., if the personal information fraud probability confidence score is below the first predetermined threshold or the second predetermined threshold), then step 251 may be performed.

At step 251, the onboarding and policy management platform 104 may finalize the onboarding process. In one or more instances, by finalizing the onboarding process, the onboarding and policy management platform 104 may cause purchase of one or more products requested by the client (e.g., insurance products/policies provided by an insurance institution). In one or more instances, in finalizing the onboarding process, the onboarding and policy management platform 104 may generate and send a notification to the client device 102 and/or the sensor device 105 that may inform a client that spot-check authentication may be periodically performed going forward to confirm the client's identity and personal information. In some instances, the onboarding and policy management platform 104 may send a notification that the client may be prompted for the same information, as provided during onboarding, once again in 24 hours to verify the client's identity. In other instances, the onboarding and policy management platform 104 might not inform the client device 102 of the spot-check authentication.

At step 252, the onboarding and policy management platform 104 may generate a digital identity signature. In one or more instances, in generating the digital identity signature, the onboarding and policy management platform 104 may generate an authentication key that may be used to initially authenticate a client with regards to the onboarding process or related verification tests. In one or more instances, the onboarding and policy management platform 104 may generate the digital identity signature based on previously received onboarding identification inputs that the onboarding and policy management platform 104 deemed to correspond accurately to the client. Additionally or alternatively, the onboarding and policy management platform 104 may generate the digital identity signature based on client identification information stored at the client verification database 106 that corresponds to the client. Additionally or alternatively, the onboarding and policy management platform 104 may direct the client device 102 or the sensor device 105 to prompt the user for the digital identity signature (e.g., "Please record words or numbers that may be used to verify your identity going forward," or the like). This may be similar to prompting a user to establish a user name and password that may be used for future authentication. Additionally, this may allow the onboarding and policy management platform 104 to verify that the client is a living individual rather than an automated robot. Additionally or alternatively, patterns of heart rate rise and fall over the course of a particular activity may be used as the digital identity signature. In yet another example, pressure sensors in the client's running shoes may be used to establish the digital identity signature. Accordingly, it should be understood that the digital identity signature may be any data/information or combination thereof that may be used to initially authenticate the client for further interactions.

Additionally or alternatively, the onboarding and policy management platform 104 may generate the digital identity signature by generating one or more questions that only the client knows the answer to. For example, the onboarding and policy management platform 104 may access data stored at the client verification database 106 corresponding to internal database information (e.g., vehicle color, house color, additional vehicle information, square footage of house, or the like) and may generate the one or more questions based on this information. For example, the digital identity signature may correspond to the internal database information, and the client may later be prompted to input this internal database information in response to the one or more questions (e.g., show an image of three vehicles and the user has to pick the right one, or the like). Additionally or alternatively, the onboarding and policy management platform 104 may access data stored at the client verification database 106 (e.g., social media information or the like) and may generate the one or more questions based on this information. For example, the digital identity signature may correspond to answers about a recent trip to Hawaii the client took (e.g., it may be determined that the client was in Hawaii based on their social media posts). Additionally or alternatively, the onboarding and policy management platform 104 may determine, based on GPS data, a popular destination of the client (e.g., a school, a business, a coffee shop, a grocery store close to the house, or the like), and may generate the one or more questions based on this information.

At step 253, the onboarding and policy management platform 103 may send the digital identity signature determined at step 252 to the mitigation analysis and output generation platform 103. In one or more instances, the onboarding and policy management platform 104 may send the digital identity signature to the mitigation analysis and output generation platform via the communication interface 116 and while the third wireless data connection is established. Additionally or alternatively, the onboarding and policy management platform 103 may send the digital identity signature to the client verification database 106.

At step 254, the mitigation analysis and output generation platform 103 may receive and store the digital identity signature sent at step 227. In one or more instances, the mitigation analysis and output generation platform 103 may receive the digital identity signature via the communication interface 113 and while the third wireless data connection is established. Alternatively, the client verification database 106 may receive and store the digital identity signature, and the mitigation analysis and output generation platform 103 may retrieve the digital identity signature from the client verification database 106.

Figure 2I:
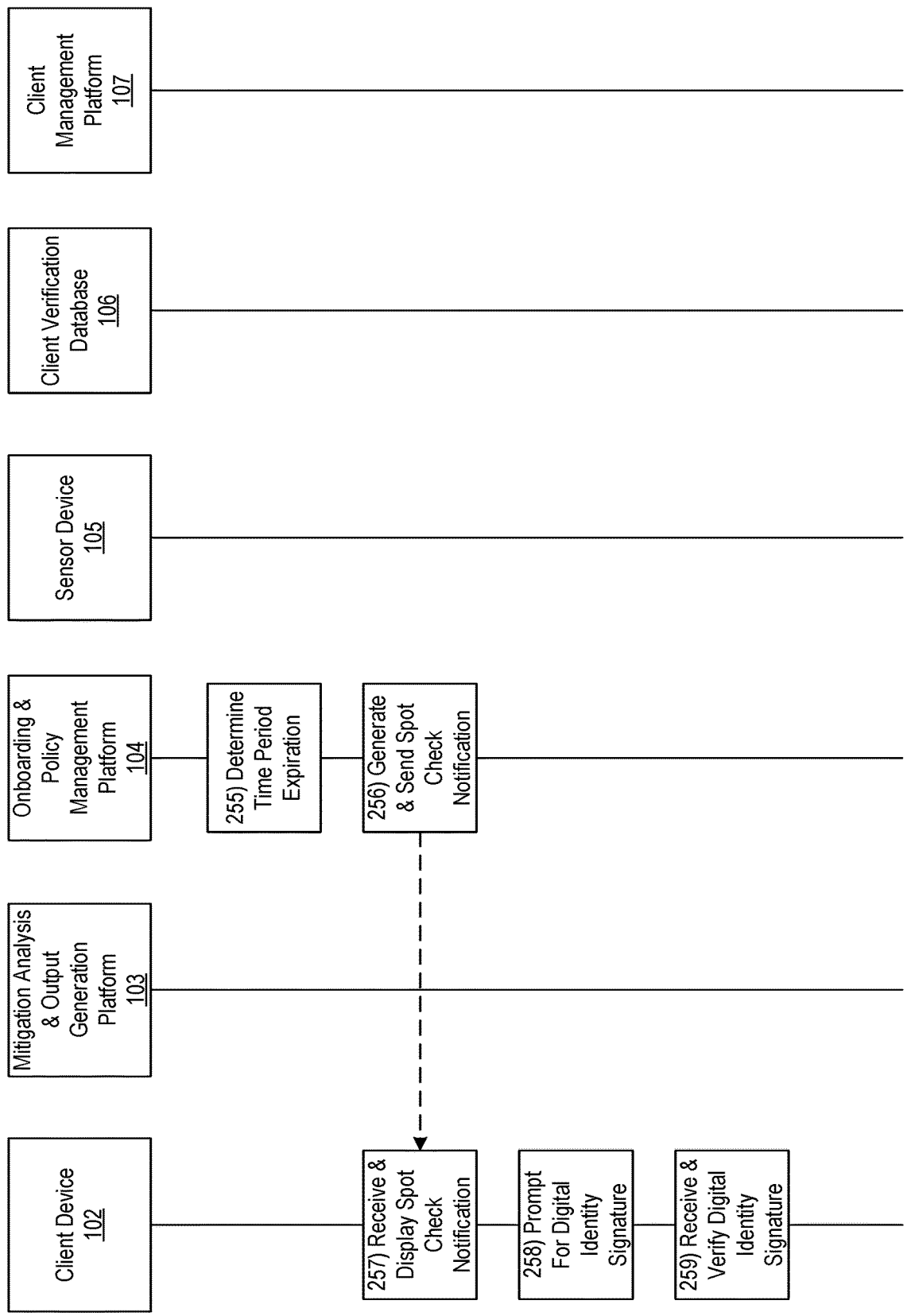

Referring to FIG. 2I, at step 255, the onboarding and policy management platform 104 may determine that a predetermined time period has expired since completion of the onboarding process at step 251. In one or more instances, the predetermined time period may be determined based on a type of product purchased during the onboarding process. In one or more instances, the predetermined time period may be randomly generated. In one or more instances, in determining the expiration of the time period, the onboarding and policy management platform 104 may compare an elapsed time since onboarding completion to a predetermined time threshold. In one or more instances, the predetermined time period may be less than a contestability period (e.g., two years).

At step 256, the onboarding and policy management platform 104 may generate and send a spot-check notification to the client device 102 based on the determination of the time period expiration at step 255. For example, the onboarding and policy management platform 104 may inform the client device 102 that further verification testing may be performed to verify client identity and personal information. In some instances, the client might not be aware of the potential for this further verification testing and/or might not be aware of when the testing will occur (e.g., this spot-check verification testing may be a surprise to the client). In one or more instances, the onboarding and policy management platform 104 may send the spot-check notification via the communication interface 116 and while the first wireless data connection is established. In one or more instances, in addition to the spot-check notification, the onboarding and policy management platform 104 may generate and send one or more commands directing the client device 102 to display the spot-check verification notification. In addition to or instead of the spot-check notification, a voice call session may be established between the client device 102 and the client management platform 107 during which an employee corresponding to the client management platform 107 may inform a client of the spot-check verification testing to be performed.

At step 257, the client device 102 may receive and display the spot-check notification sent at step 256. In one or more instances, the client device 102 may receive the spot-check notification while the first wireless data connection is established. In one or more instances, in addition to the spot-check notification, the client device 102 may receive one or more commands directing the client device 102 to display the spot-check verification notification. In one or more instances, in displaying the spot-check notification, the client device 102 may display a graphical user interface similar to graphical user interface 805, which is displayed in FIG. 8A. For example, the graphical user interface 805 may indicate to a client that a spot-check verification test will be performed, and may prompt the client to accept. In one or more instances, a temporary hold may be placed on the client's account until they accept/complete the spot-check verification test. In one or more instances, the "accept" button may corresponding to a link to the spot-check verification test.

At step 258, the client device 102 may prompt for the digital identity signature generated at step 252. In prompting for the digital identity signature, the client device 102 may prompt a client for an initial authentication measure.

At step 259, the client device 102 may receive and verify the digital identity signature. In one or more instances, the client device 102 may communicate with the mitigation analysis and output generation platform 103 to compare the received digital identity signature to the stored digital identity signature. In one or more instances, the client device 102 may retrieve the stored digital identity signature from the mitigation analysis and output generation platform 103 or the client verification database 106. If the client device 102 determines that the digital identity signature exceeds a predetermined correlation threshold with the stored digital identity signature, the client device 102 may proceed. Otherwise, the client device 102 may prompt the client to re-enter the digital identity signature. In one or more instances, the client device 102 may verify the digital identity signature using one or more machine learning algorithms.

Figure 2J:
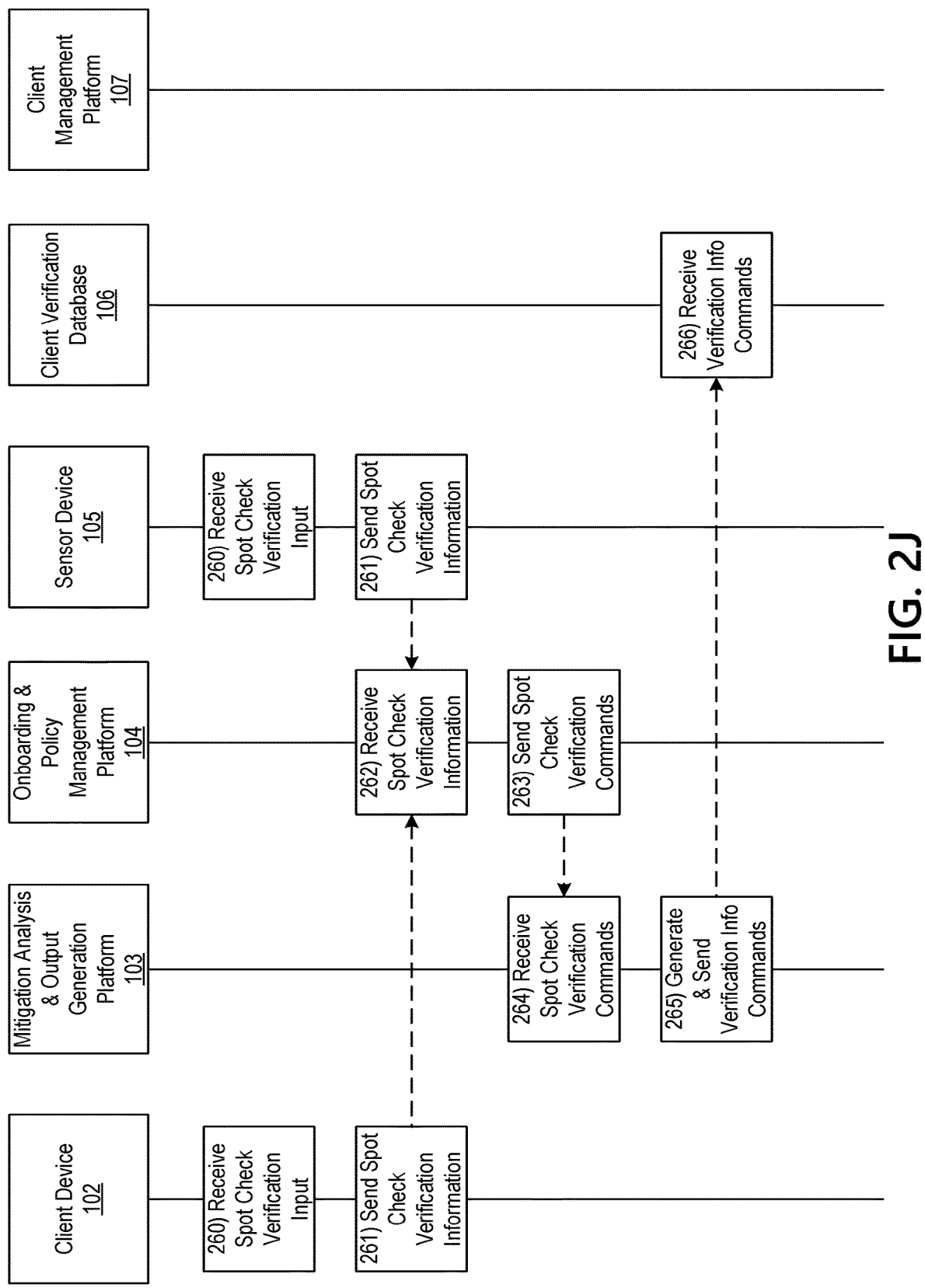

Referring to FIG. 2J, at step 260, once the digital identity signature has been received and verified, the client device 102 and/or the sensor device 105 may prompt for and receive a spot-check verification input. In receiving the spot-check verification input, the client device 102 and/or the sensor device 105 may receive information indicative of a user identity or personal information. In one or more instances, in receiving the spot-check verification input, the client device 102 and/or the sensor device 105 may receive one or more of a pulse, a voice signature, a motion signature, (e.g., walking, running, or the like), a fingerprint, a code response, or the like for verifying the client's identity. In one or more instances, in receiving the spot-check verification input, the client device 102 and/or the sensor device 105 may retrieve personal data, such as health data, fitness/activity data, location data, purchase history data, credit history data, MVRs data, MIB data, medical billing records data, social networking data, etc. for verifying the client's personal information. Additionally or alternatively, the client device 102 and/or the sensor device 105 may receive any of the other pieces of information described above with regard to the onboarding identification inputs at step 203 and the onboarding personal information at step 232 and may employ any similar techniques as described above (e.g., microphone/infrared detection or the like). In one or more instances, the client device 102 may indicate what spot-check verification input should be received. In one or more instances, the client device 102 and/or the sensor device 105 may prompt for a particular type of spot-check verification input based on known sensor devices 105 corresponding to the client device 102. For example, if the client has a fitness tracker band, the client device 102 and/or the sensor device 105 may be more likely to prompt for a motion signature. Additionally or alternatively, the client device 102 and/or the sensor device 105 may establish a video call session with the client management platform 107, and the spot-check verification inputs may be received while the video call session is established. For example, a client may be prompted to move the client device 102 and/or the sensor device 105 around and in particular angles. Accordingly, the client device 102 and/or the sensor device 105 may collect photographs of the client or of the background, and this information may be further analyzed as described below.

Although the spot-check verification process is described herein following the onboarding process, it should be understood that in some instances, spot-check verification may be performed significantly after or without the onboarding process (e.g., for existing customers). In these instances, spot-check verification may be performed regardless of whether or not the initial onboarding process occurs.

At step 261, the client device 102 and/or the sensor device 105 may send spot-check verification information, based on the spot-check verification inputs received at step 260, to the onboarding and policy management platform 104. In one or more instances, the client device 102 and the sensor device 105 may send the spot-check verification information while the first and second wireless data connections, respectively, are established. In one or more instances, the spot-check verification information may be similar to the information described above with regard to steps 204 and 232. Additionally, or alternatively, the spot-check verification information may include an amount of time elapsed during the onboarding process.

At step 262, the onboarding and policy management platform 104 may receive the spot-check verification information sent at step 261. In one or more instances, the onboarding and policy management platform 104 may receive the spot-check verification information via the communication interface 116 and while the first and second wireless data connections are established.

At step 263, the onboarding and policy management platform 104 may generate and send one or more spot-check verification commands directing the mitigation analysis and output generation platform 103 to analyze the spot-check verification information received at step 262. In one or more instances, the onboarding and policy management platform 104 may send the spot-check verification information along with the spot-check verification commands. In one or more instances, the onboarding and policy management platform 104 may send, via the communication interface 116 and while the third wireless data connection is established, the one or more spot-check verification commands directing the mitigation analysis and output generation platform 103 to analyze the spot-check verification information.

At step 264, the mitigation analysis and output generation platform 103 may receive the one or more spot-check verification commands directing the mitigation analysis and output generation platform 103 to analyze the spot-check verification information. In one or more instances, the mitigation analysis and output generation platform 103 may receive, via the communication interface 113 and while the third wireless data connection is established, the one or more spot-check verification commands directing the mitigation analysis and output generation platform 103 to analyze the spot-check verification information. In these instances, the mitigation analysis and output generation platform 103 may receive commands to compare the spot-check verification information to stored client verification information that corresponds to anticipated values for the spot-check verification information.

At step 265, the mitigation analysis and output generation platform 103 may generate and send one or more commands directing the client verification database 106 to determine and send client verification information corresponding to the client. In one or more instances, the mitigation analysis and output generation platform 103 may send the one or more commands directing the client verification database 106 to determine and send client verification information corresponding to the client via the communication interface 113 and while the fourth wireless data connection is established. In one or more instances, the mitigation analysis and output generation platform 103 may send a device identifier corresponding to the client device 102 along with the commands.

At step 266, the client verification database 106 may receive the one or more commands directing the client verification database 106 to determine and send client verification information corresponding to the client. In one or more instances, the client verification database 106 may receive the one or more commands directing the client verification database 106 to determine and send client verification information corresponding to the client while the fourth wireless data connection is established.

Figure 2K:
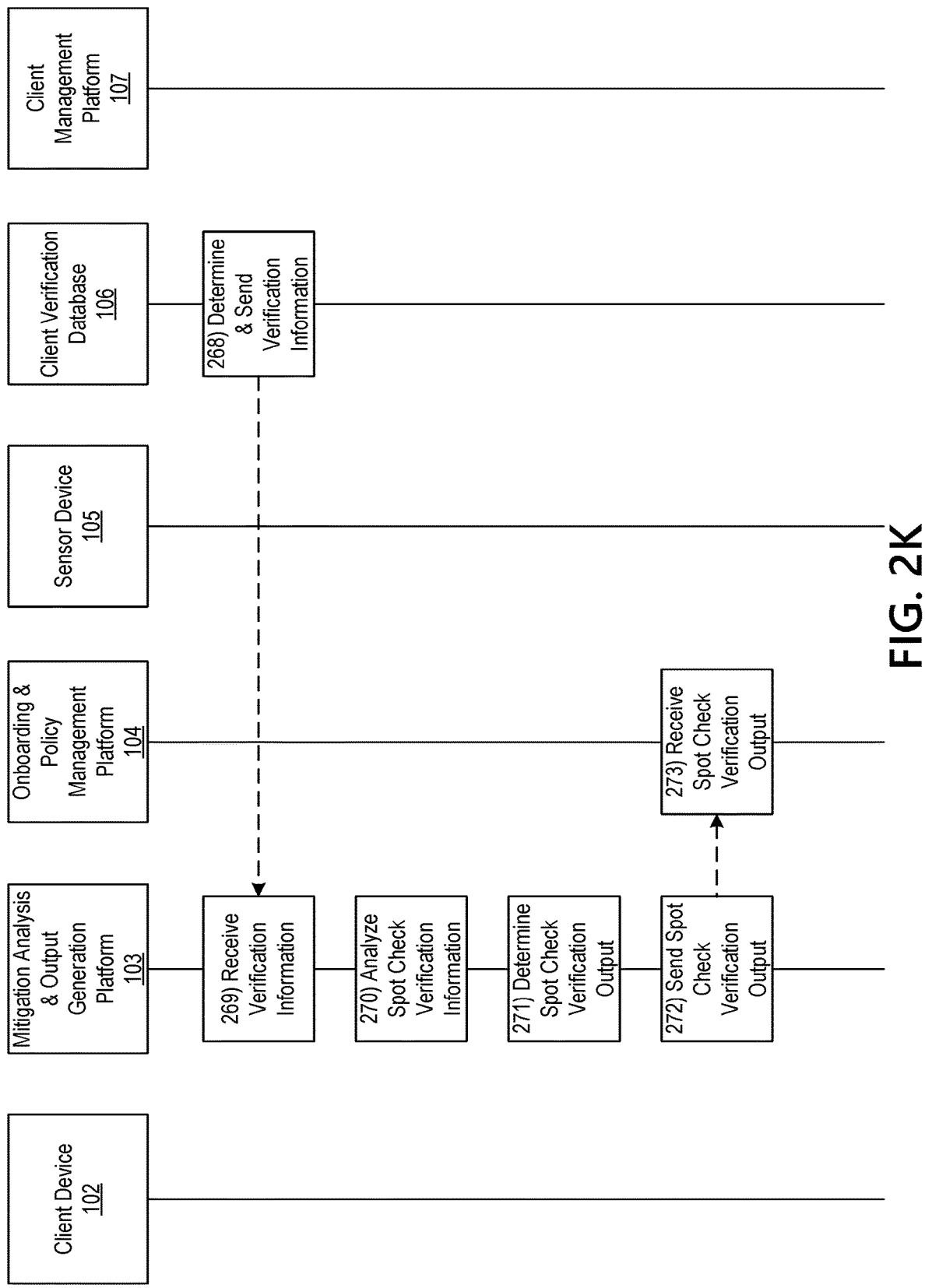

Referring to FIG. 2K, at step 268, the client verification database 106 may determine and send client verification information corresponding to the client. In one or more instances, the client verification database 106 may determine the relevant client verification information in a similar manner to that described above with regard to step 211. In one or more instances, the client verification database 106 may send the client verification information corresponding to the client while the fourth wireless data connection is established.

At step 269, the mitigation analysis and output generation platform 103 may receive the client verification information from the client verification database 106. In one or more instances, the mitigation analysis and output generation platform 103 may receive the client verification information via the communication interface 113 and while the fourth wireless data connection is established.

At step 270, the mitigation analysis and output generation platform 103 may analyze the spot-check verification information. In one or more instances, the mitigation analysis and output generation platform 103 may compare the spot-check verification information to the client verification information. The analysis performed by the mitigation analysis and output generation platform 103 at step 270 may be similar to the analysis performed at step 213 with regard to the onboarding identification information and step 240 with regard to the onboarding personal information. In one or more instances, the mitigation analysis and output generation platform 103 may determine a correlation between the amount of time elapsed during the spot-check verification process and an anticipated amount of time to complete the spot-check verification process. In these instances, the anticipated amount of time may be based on the particular product type of the product purchased during the onboarding, as identified above as step 202. In one or more instances, the mitigation analysis and output generation platform 103 may analyze the spot-check verification information using one or more machine learning algorithms and datasets. In one or more instances, the mitigation analysis and output generation platform 103 may compare the spot-check verification information to the onboarding identification information and the onboarding personal information received at steps 205 and 233. It should be understood that analysis of the spot-check verification information at step 270 may be similar to the analysis of the onboarding identification information at steps 213 and 240.

At step 271, based on the analysis performed at step 270, the mitigation analysis and output generation platform 103 may generate a spot-check verification output to quantify a correlation between the spot-check verification information and the onboarding identification information and the onboarding personal information. In one or more instances, in determining the spot-check verification output, the mitigation analysis and output generation platform 103 may generate a spot-check score between 0 and 100 with 100 being the highest likelihood of a fraud event and 0 being the lowest likelihood of a fraud event. Accordingly, in generating the spot-check verification output, the mitigation analysis and output generation platform 103 may generate an indication of a correlation between the received spot-check verification inputs and expected spot-check verification inputs. Similarly, in generating the spot-check verification output, the mitigation analysis and output generation platform 103 may generate a likelihood that mitigation techniques should be used.

At step 272, the mitigation analysis and output generation platform 103 may send the spot-check verification output, determined at step 271, to the onboarding and policy management platform 104. In one or more instances, the mitigation analysis and output generation platform 103 may send the spot-check verification output to the onboarding and policy management platform 104 via the communication interface 113 and while the third wireless data connection is established.

At step 273, the onboarding and policy management platform 104 may receive the spot-check verification output sent at step 272. In one or more instances, the onboarding and policy management platform 104 may receive the spot-check verification output via the communication interface 116 and while the fourth wireless data connection is still established.

Figure 2L:
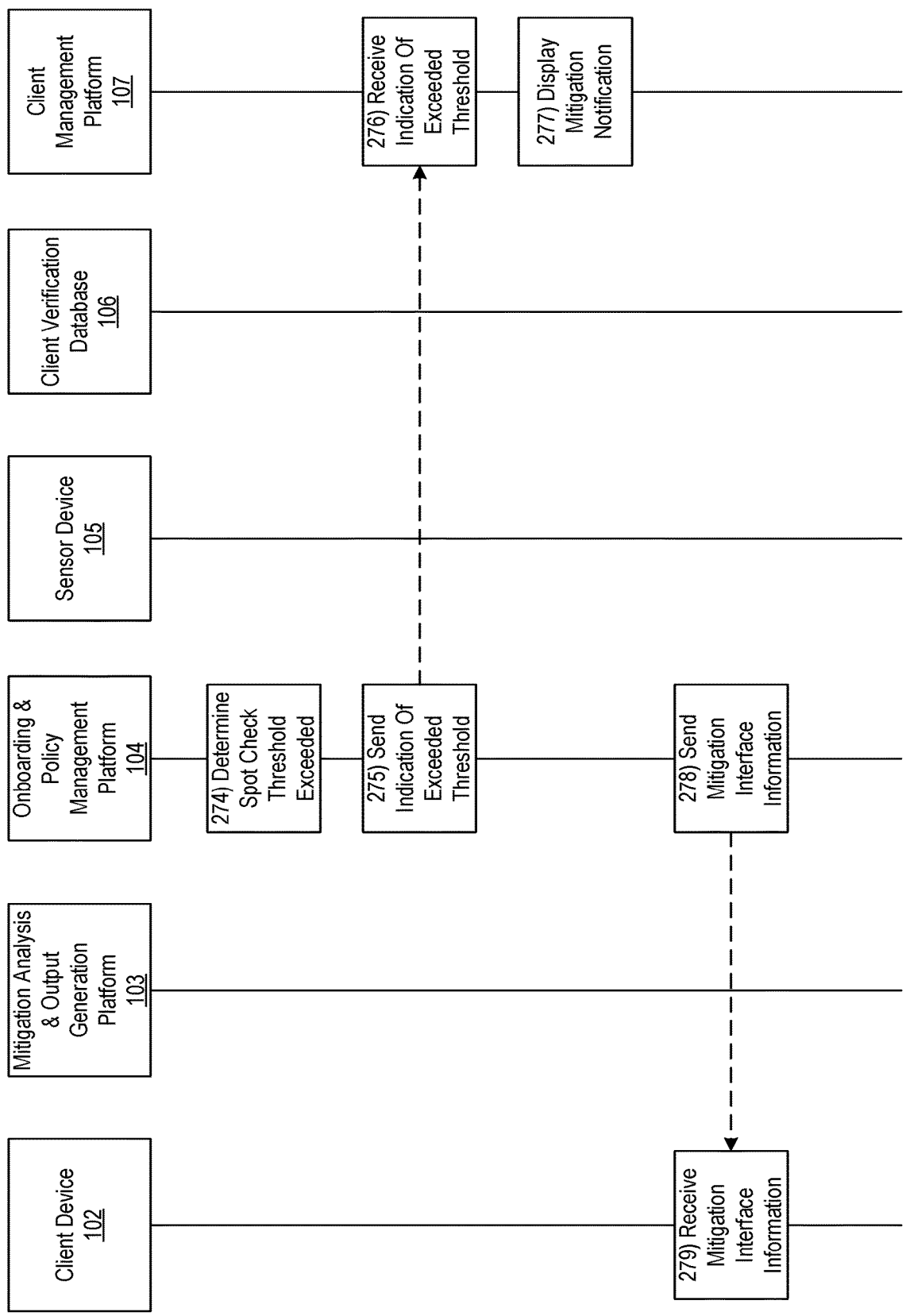

Referring to FIG. 2L, at step 274, the onboarding and policy management platform 104 may determine whether the spot-check verification output exceeds a predetermined spot-check threshold. In one or more instances, the onboarding and policy management platform 104 may determine the predetermined spot-check threshold based on a type of the product purchased during the onboarding process. For example, the onboarding and policy management platform 104 may impose a higher level of security on certain purchases than on others. In one or more instances, the predetermined spot-check threshold may correspond to the predetermined mitigation thresholds described above at step 217 or 244. In other instances, the predetermined spot-check threshold may be different than the predetermined mitigation thresholds described at step 217 or 244. If the onboarding and policy management platform 104 determines that the spot-check verification output does not exceed the predetermined spot-check threshold, the client identity and personal information may be verified and the event sequence may end. If the onboarding and policy management platform 104 determines that the spot-check verification output does exceed the predetermined spot-check threshold, the onboarding and policy management platform 104 may proceed to step 275.

At step 275, the onboarding and policy management platform 104 may generate and send an indication of the exceeded spot-check threshold. In one or more instances, the onboarding and policy management platform 104 may send the indication of the exceeded spot-check threshold to the client management platform 107 via the communication interface 116 and while the fifth wireless data connection is established. In one or more instances, the onboarding policy management platform 104 may also generate one or more commands directing the client management platform 107 to display a mitigation notification based on the indication of the exceeded spot-check threshold, and may send the one or more commands to the client management platform 107 along with the indication of the exceeded spot-check threshold.

At step 276, the client management platform 107 may receive the indication of the exceeded spot-check threshold and the one or more commands directing the client management platform 107 to display the mitigation notification based on the indication of the exceeded spot-check threshold. In one or more instances, the client management platform 107 may receive the indication of the exceeded spot-check threshold and the one or more commands while the fifth wireless data connection is established.

At step 277, the client management platform 107 may display the mitigation notification. In one or more instances, in displaying the mitigation notification, the client management platform 107 may display a graphical user interface similar to graphical user interface 810, which is shown in FIG. 8B. For example, the client management platform 107 may display an indication that the client failed the spot-check verification test, and may prompt for user input on whether the product corresponding to the onboarding process should be cancelled (e.g., cancel the policy, or the like), or whether the client should be prompted for additional spot-check verification inputs. In one or more instances, if the client management platform 107 receives a user input indicating that the product should be cancelled, the client management platform 107 may send an indication to the onboarding and policy management platform 104 that the purchase of the product should be voided.

At step 278, based on the determination at step 274 that the spot-check threshold was exceeded, the onboarding and policy management platform 104 may generate and send mitigation interface information to the client device 102 along with one or more commands directing the client device 102 to generate and display a spot-check verification interface. In one or more instances, the onboarding and policy management platform 104 may send, via the communication interface 116 and while the first wireless data connection is established, the mitigation interface information and the one or more commands directing the client device 102 to generate and display the spot-check verification interface.

At step 279, the client device 102 may receive the mitigation interface information and the one or more commands directing the client device 102 to generate and display the spot-check verification interface. In one or more instances, the client device 102 may receive the mitigation interface information and the one or more commands directing the client device 102 to generate and display the spot-check verification interface while the first wireless data connection is established.

Referring to FIG. 2M, at step 280, the client device 102 may generate and display the spot-check verification interface based on the mitigation interface information received at step 279. In generating the spot-check verification interface, the client device 102 may generate and display an interface that prompts the client for additional spot-check verification inputs. In one or more instances, in displaying the spot-check verification interface, the client device 102 may display an indication that an in person interview will be conducted, and may prompt the client to input scheduling information.

Additionally or alternatively, the client device 102 may display an indication that an in person test to obtain the spot-check verification inputs may be conducted. For example, if blood pressure data was received at step 260, the client device 102 may display an indication that an in person blood pressure test should be conducted within a predetermined period of time (e.g., 2 weeks). In this example, the client device 102 may provide options of one or more facilities at which the testing may be performed (e.g., minute clinics, doctors, or the like). In some examples, the client device 102 may display an indication that additional in person testing should be conducted, but might not provide an indication of the type of testing (e.g., may keep this as a surprise to the client to reduce the client's ability to cheat on the testing).

Additionally or alternatively, the client device 102 may establish a video call session with the client management platform 107.

At step 281, the client device 102 and/or the sensor device 105 may receive the additional spot-check verification inputs. Once the additional spot-check verification inputs are received, the event sequence may return to step 261 to initiate analysis of the additional spot-check verification inputs. In one or more instances, the additional spot-check verification inputs may be similar to the information received at steps 203, 232, and/or 260, which are described above.

Once the additional spot-check verification inputs are verified, the example event sequence may end, and the mitigation analysis and output generation platform 103 and onboarding and policy management platform 104 may continue to analyze the authenticity of clients during and after an onboarding process is conducted. By operating in this way, these computing platforms may increase security associated with the onboarding process and may allow individuals and entities who manage the onboarding process to more effectively mitigate fraud by ensuring that an individual providing the client identification inputs and personal information during the onboarding process is the individual who they purport to be (e.g., they are not using a surrogate individual to perform the tests, such as in the case where an out of shape parent has their athlete child perform fitness tests during onboarding to obtain better coverage and/or rates).

While the mitigation analysis and output generation platform 103, the onboarding policy management platform 104, client verification database 106, and client management platform 107 are shown and described as separate devices, in some instances, these may be embodied in a single device.

Figure 3:
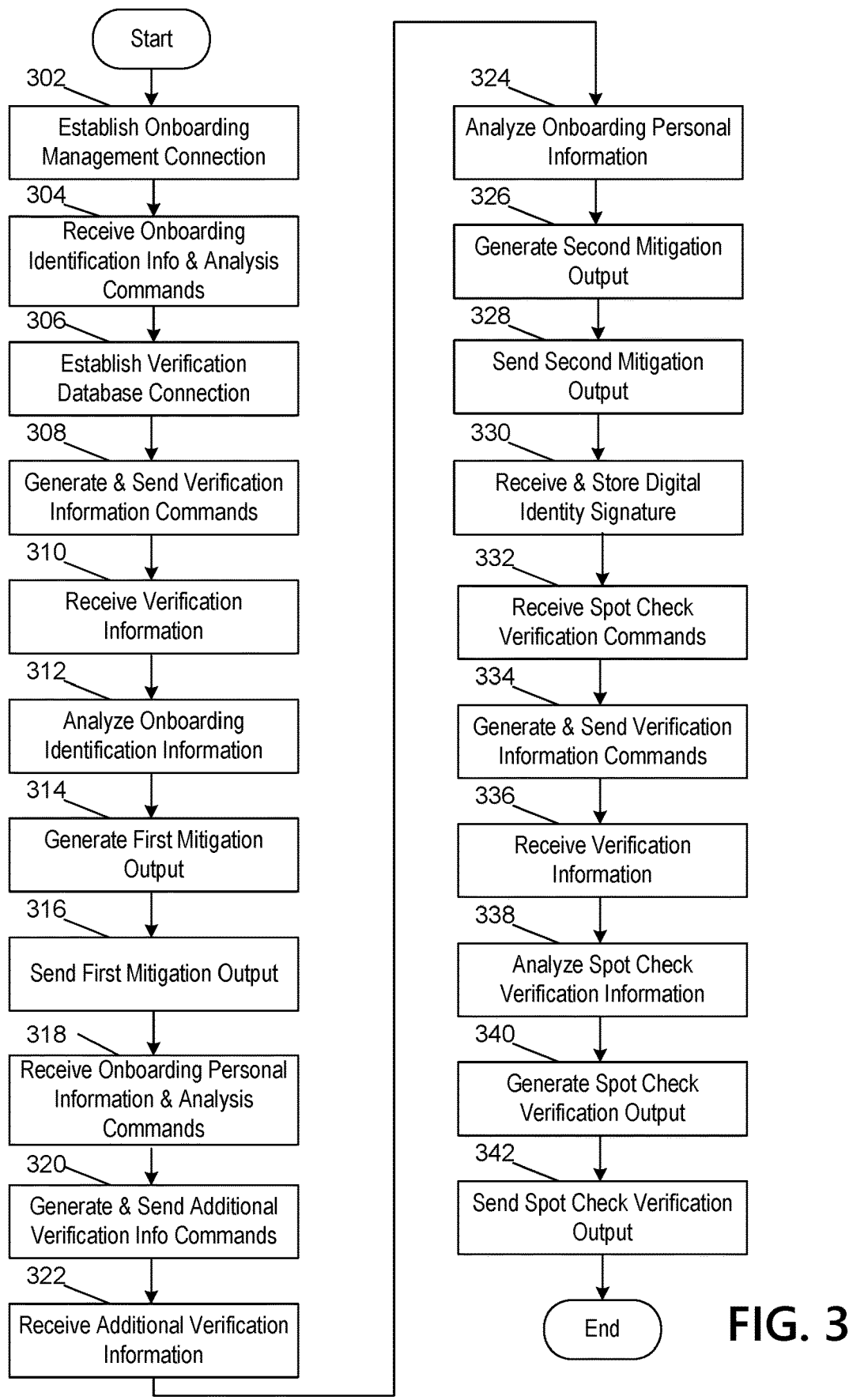
FIGS. 3 and 4A-4B depict illustrative methods for deploying computing platforms that utilize improved mitigation analysis and policy management techniques in accordance with one or more example arrangements discussed herein.

FIG. 3 depicts an illustrative method for deploying a mitigation analysis and output generation platform 103 that utilizes improved techniques to analyze onboarding and spot-check verification information in accordance with one or more example embodiments. Referring to FIG. 3, at step 302, a computing platform (such as mitigation analysis and output generation platform 103) may establish a connection with an onboarding and policy management computing platform (such as onboarding and policy management computing platform 103). At step 304, the computing platform may receive onboarding identification information and one or more commands directing the computing platform to analyze the onboarding identification information. At step 306, the computing platform may establish a connection with a client verification database (such as client verification database 106). At step 308, the computing platform may generate and send one or more commands directing the client verification database to provide client verification information. At step 310, the computing platform may receive the client verification information. At step 312, the computing platform may use the client verification information to analyze the onboarding identification information. At step 314, the computing platform may generate a first mitigation output based on the analysis. At step 316, the computing platform may send the first mitigation output to the onboarding and policy management computing platform. The first mitigation output may include a first fraud probability confidence score. At step 318, the computing platform may the receive the onboarding personal information (e.g., the health data, fitness/activity data, location data, purchase history data, credit history data, MVRs data, MIB data, medical billing records data, social networking data, etc.) and one or more commands directing the computing platform to analyze the onboarding personal information. At step 320, the computing platform may generate and send one or more commands directing the client verification database to provide additional client verification information. At step 322, the computing platform may receive the additional client verification information. At step 324, the computing platform may use the additional client verification information to analyze the onboarding personal information. At step 326, the computing platform may generate a second mitigation output based on the analysis. The second mitigation output may include a second fraud probability confidence score. At step 328, the computing platform may send the second mitigation output to the onboarding and policy management computing platform. At step 330, the computing platform may receive and store a digital identity signature. At step 332, the computing platform may receive one or more commands directing the computing platform to perform verification of one or more spot-check verification inputs. At step 334, the computing platform may generate and send one or more commands directing the client verification database to provide client verification information. At step 336, the computing platform may receive the client verification information. At step 338, the computing platform may analyze the spot-check verification information by comparing it to the client verification information. At step 340, the computing platform may generate a spot-check verification output based on the analysis. The spot-check verification output may include a spot-check score. At step 342, the computing platform may send the spot-check verification output to the onboarding and policy management computing platform.

Figure 4A:
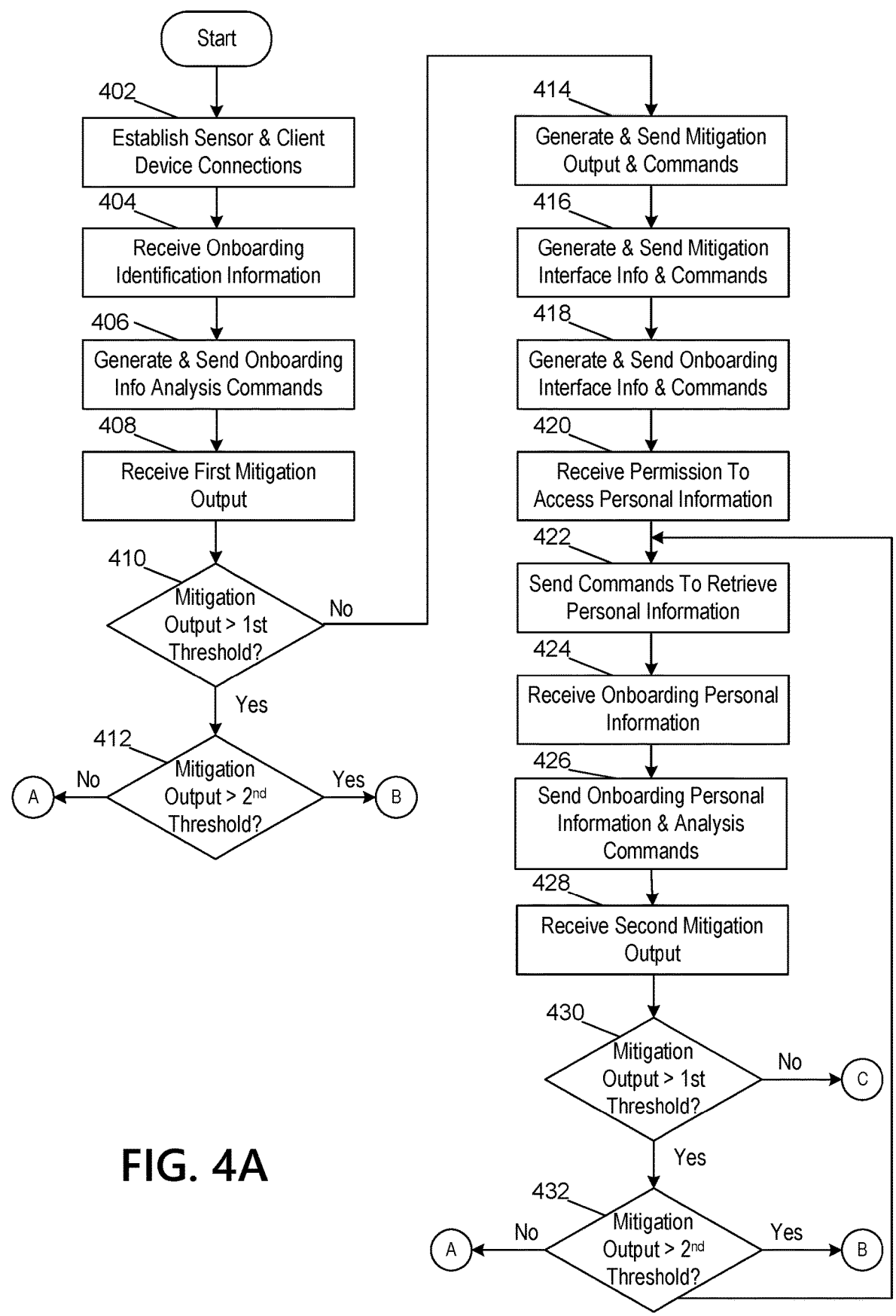
Figure 4B:
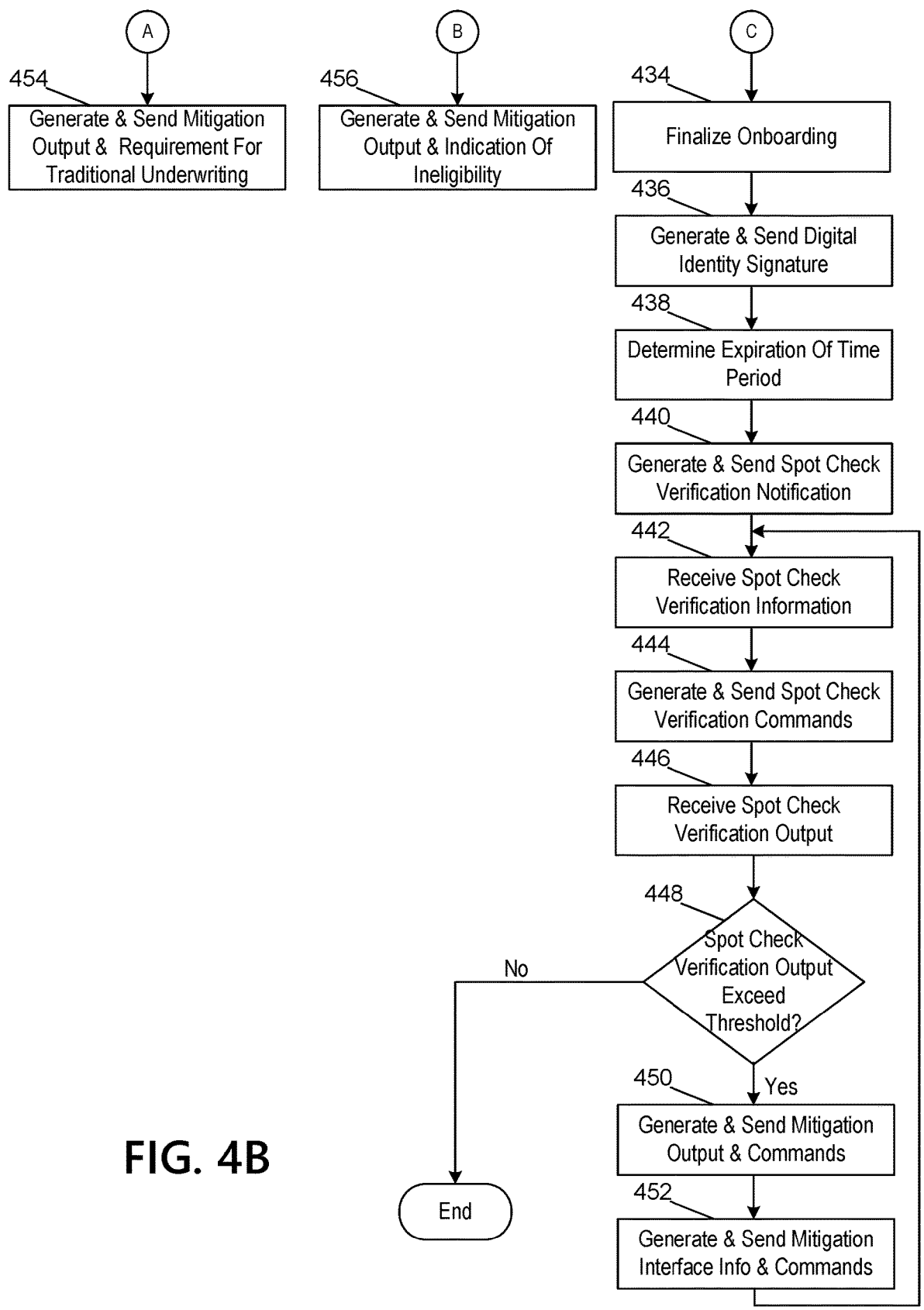

FIGS. 4A-4B depicts an illustrative method for deploying an onboarding and policy management platform 104 that utilizes improved techniques to manage onboarding processes and established policies in accordance with one or more example embodiments. Referring to FIG. 4A, at step 402, the computing platform (such as the onboarding and policy management platform 104) may establish a connection to a client device (such as client device 102) and a sensor device (such as sensor device 105). At step 404, the computing platform may receive onboarding identification information from the sensor device and/or the client device. At step 406, the computing platform may establish a connection with a mitigation analysis and output generation platform (such as the mitigation analysis and output generation platform 103) and may generate and send one or more commands directing the mitigation analysis and output generation platform to analyze the onboarding identification information. At step 408, the computing platform may receive a first mitigation output based on the analysis. The first mitigation output may include a first fraud probability confidence score. At step 410, the computing platform may determine whether the first mitigation output exceeds a first identification information mitigation threshold. If the first mitigation output does not exceed the first identification information mitigation threshold, the computing platform may proceed to step 414 to continue with the onboarding process. If the first mitigation output does exceed the first identification information mitigation threshold, the computing platform may proceed to step 412 to determine if the first mitigation output also exceeds a second identification information mitigation threshold. At step 412, the computing platform may determine whether the first mitigation output exceeds the second identification information mitigation threshold. If the first mitigation output does not exceed the second identification information mitigation threshold (but exceeded the first identification information mitigation threshold in step 410), the computing platform may proceed to step 454. If the first mitigation output exceeds the second identification information mitigation threshold, the computing platform may proceed to step 456. At step 414, the computing platform may establish a connection with a client management platform (such as client management platform 107) and may generate and send one or more commands directing the client management platform to display the mitigation output. At step 416, the computing platform may generate and send mitigation interface information and one or more commands directing the client device and/or the sensor device to display a mitigation interface. At step 418, the computing platform may generate and send onboarding interface information and one or more commands directing the client device and/or the sensor device to display an onboarding interface for collecting onboarding personal information, such as health, fitness/activity, location, and other information. At step 420, the computing platform may receive permission to collect, access, analyze and/or process the client's personal information, such as health, fitness/activity, location, and/or other information related to the client. At step 422, the computing platform may send, to the client device, the sensor device, or one or more external data sources, one or more commands to retrieve the onboarding personal information as specified by the permissions. At step 424, the computing platform may receive the onboarding personal information sent from the client device, the sensor device, or the one or more external data sources. At step 426, the computing platform may generate and send one or more commands directing the mitigation analysis and output generation platform to analyze the onboarding personal information. The computing platform may send the onboarding personal information together with the one or more commands. At step 428, the computing platform may receive a second mitigation output from the mitigation and output generation platform based on the analysis of the onboarding personal information. The second mitigation output may include a second fraud probability confidence score. At step 430, the computing platform may determine whether the second mitigation output exceeds a first personal information mitigation threshold. If the second mitigation output does not exceed the first personal information mitigation threshold, the computing platform may proceed to step 434 to finalize the onboarding process. If the mitigation output exceeds the first personal information mitigation threshold, the computing platform may proceed to step 432 to determine if the mitigation output also exceeds a second personal information mitigation threshold. At step 432, the computing platform may determine whether the second mitigation output exceeds the second personal information mitigation threshold. If the second mitigation output does not exceed the second personal information mitigation threshold (but exceeded the first personal information mitigation threshold in step 430, the computing platform may proceed to step 454. If the second mitigation output exceeds the second personal information mitigation threshold, the computing platform may proceed to step 456. Referring to FIG. 4B, at step 434, the computing platform may finalize the onboarding process. At step 436, the computing platform may generate and send a digital identity signature to the mitigation analysis and output generation platform. At step 438, the computing platform may determine that a predetermined period of time since completion of the onboarding process has elapsed. At step 440, the computing platform may generate and send a spot-check verification notification to the client device. At step 442, the computing platform may receive spot-check verification information. At step 444, the computing platform may generate and send one or more commands directing the mitigation analysis and output generation platform to analyze the spot-check verification information. At step 446, the computing platform may receive a spot-check verification output. The spot-check verification output may include a spot-check score. At step 448, the computing platform may determine whether the spot-check verification output exceeds a predetermined threshold. If the spot-check verification output does not exceed the predetermined threshold, the method may end. If the spot-check verification output does exceed the predetermined threshold, the computing platform may proceed to step 450. At step 450, the computing platform may generate and send one or more commands for the client management platform to display the mitigation output. At step 452, the computing platform may generate and send mitigation interface information, and one or more commands directing the client device to display a mitigation interface based on the mitigation interface information. The computing platform may then return to step 442 to receive additional spot-check verification information. At step 454, the computing platform may generate and send to the client management platform, the client device and/or the sensor device mitigation output and indication that the client will require undergoing traditional underwriting in order to determine eligibility. At step 456, the computing platform may generate and send to the client management platform, the client device and/or the sensor device mitigation output and an indication that the client is ineligible for the requested product. One or more aspects of the disclosure may be embodied in computer-usable data or computer-executable instructions, such as in one or more program modules, executed by one or more computers or other devices to perform the operations described herein. Generally, program modules include routines, programs, objects, components, data structures, and the like that perform particular tasks or implement particular abstract data types when executed by one or more processors in a computer or other data processing device. The computer-executable instructions may be stored as computer-readable instructions on a computer-readable medium such as a hard disk, optical disk, removable storage media, solid-state memory, RAM, and the like. The functionality of the program modules may be combined or distributed as desired in various embodiments. In addition, the functionality may be embodied in whole or in part in firmware or hardware equivalents, such as integrated circuits, application-specific integrated circuits (ASICs), field programmable gate arrays (FPGA), and the like. Particular data structures may be used to more effectively implement one or more aspects of the disclosure, and such data structures are contemplated to be within the scope of computer executable instructions and computer-usable data described herein.

Various aspects described herein may be embodied as a method, an apparatus, or as one or more computer-readable media storing computer-executable instructions. Accordingly, those aspects may take the form of an entirely hardware embodiment, an entirely software embodiment, an entirely firmware embodiment, or an embodiment combining software, hardware, and firmware aspects in any combination. In addition, various signals representing data or events as described herein may be transferred between a source and a destination in the form of light or electromagnetic waves traveling through signal-conducting media such as metal wires, optical fibers, or wireless transmission media (e.g., air or space). In general, the one or more computer-readable media may be and/or include one or more non-transitory computer-readable media.

As described herein, the various methods and acts may be operative across one or more computing servers and one or more networks. The functionality may be distributed in any manner, or may be located in a single computing device (e.g., a server, a client computer, and the like). For example, in alternative embodiments, one or more of the computing platforms discussed above may be combined into a single computing platform, and the various functions of each computing platform may be performed by the single computing platform. In such arrangements, any and/or all of the above-discussed communications between computing platforms may correspond to data being accessed, moved, modified, updated, and/or otherwise used by the single computing platform. Additionally or alternatively, one or more of the computing platforms discussed above may be implemented in one or more virtual machines that are provided by one or more physical computing devices. In such arrangements, the various functions of each computing platform may be performed by the one or more virtual machines, and any and/or all of the above-discussed communications between computing platforms may correspond to data being accessed, moved, modified, updated, and/or otherwise used by the one or more virtual machines.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps depicted in the illustrative figures may be performed in other than the recited order, and one or more depicted steps may be optional in accordance with aspects of the disclosure.

What is claimed is:

1. A computing platform comprising:
an onboarding and policy management computing platform in connection with a computing device and a sensor device over a network, the onboarding and policy management computing platform receiving onboarding inputs in connection with an onboarding process from the computing device over the network, the onboarding inputs including a request to purchase a product, the onboarding and policy management computing platform sending to the computing device and based on the request to purchase the product, one or more commands to collect data from the computing device; and
a mitigation analysis and output generation computing platform receiving, in connection with the onboarding process, first data of a first type that is collected using one of a sensor of the computing device or the sensor device and second data of a second type is collected using another of the sensor of the computing device or the sensor device, the second type different from the first type, the mitigation analysis and output generation computing platform analyzing the first data and the second data for inconsistencies and determining based on the analysis of the first data and the second data, a mitigation output indicating a level of inconsistency between the first data and the second data, the level of inconsistency indicating a probability of fraud during the onboarding process, the onboarding and policy management computing platform determining, based on the mitigation output, eligibility for the requested product and generating and sending an indication of the eligibility to one or more of the computing device and the sensor device to cause one or more of the computing device and the sensor device to output the indication, wherein the first and second data are personal health data of a user of the computing device.

2. The computing platform of claim 1, wherein the personal health data includes one or more of fitness/activity data, location data, purchase history data, credit history data, motor vehicle records (MVRs) data, medical information bureau (MIB) data, medical billing records data, medical prescription data, and social networking data.

3. The computing platform of claim 1, wherein the first data comprises a count of steps taken by the user of the computing device during a first period of time and the second data comprises a heart rate of the user during the first period of time, and wherein the mitigation analysis and output generation computing platform analyzes the first data and the second data for inconsistencies by:
determining, from the first data, a first identifier identifying the computing device used to collect the first data;
determining, from the second data, a second identifier identifying the sensor device used to collect the second data;
comparing the first identifier and the second identifier; and
identifying an inconsistency, based on determining that the first identifier and the second identifier differ.

4. The computing platform of claim 1, wherein the first data comprises a count of steps taken by the user of the computing device during a first time period and the second data comprises a sleep pattern of the user during the first time period, and wherein the mitigation analysis and output generation computing platform analyzes the first data and the second data for inconsistencies by:
determining, from the first data, whether the count of steps during the first time period exceeds a predetermined threshold;
determining, from the second data, whether the sleep pattern indicates that the user was sleeping during the first time period; and
identifying an inconsistency, based on determining that the count of steps during the first time period exceeds the predetermined threshold and determining that the sleep pattern indicates that the user was sleeping during the first time period.

5. The computing platform of claim 1, wherein the first data comprises a count of steps taken by the user of the computing device during a first period of time and the second data comprises movement data associated with the computing device during the first period of time, and wherein the mitigation analysis and output generation computing platform analyzes the first data and the second data for inconsistencies by:
determining, from the first data, whether the count of steps was entered manually;
determining, from the second data, whether the movement data indicates movement at a speed greater than a predetermined threshold; and
identifying an inconsistency, based on determining that the count of steps was entered manually and the movement data indicates movement at a speed greater than the predetermined threshold.

6. The computing platform of claim 1, wherein the first data comprises a count of steps taken by the user of the computing device during a first period of time and the second data comprises movement data associated with the computing device during the first period of time, and wherein the mitigation analysis and output generation computing platform analyzes the first data and the second data for inconsistencies by:
determining, from the first data, whether the count of steps exceeds a first predetermined threshold;
determining, from the second data, whether the movement data deviates from average movement data by more than a second predetermined threshold; and
identifying an inconsistency, based on determining that the count of steps exceeds the first predetermined threshold and the movement data deviates from the average movement data by more than the second predetermined threshold.

7. The computing platform of claim 1, wherein the first data comprises purchase history data and the second data comprises device location data associated with the computing device or sensor device, and wherein the mitigation analysis and output generation computing platform analyzes the first data and the second data for inconsistencies by:
determining, from the first data, information related to a prescription purchase by the user of the computing device;
determining, from the information related to the prescription purchase, a purchase date and a purchase location;
determining, from the second data, device location information for the purchase date;
comparing the device location information with the purchase location; and
identifying an inconsistency, based on determining that the device location information does not match the purchase location for the purchase date.

8. The computing platform of claim 1, wherein the mitigation output includes a fraud probability confidence score determined based on the analysis of the first data and the second data.

9. One or more tangible non-transitory computer-readable storage media storing computer-executable instructions for performing a computer process on a computing system, the computer process comprising:
receiving a request to purchase a product from a computing device at an onboarding and policy management platform;
sending, to the computing device and based on the request to purchase the product, one or more commands to display a request for permission to collect data from a first data source and a second data source;
retrieving, from the first data source, first data of a first type, wherein the first data source is a database;

retrieving, from the second data source, second data of a second type different from the first type, wherein the second data source comprises a sensor associated with the computing device;

analyzing the first data and the second data for inconsistencies using a mitigation analysis and output generation platform;

determining using the mitigation analysis and output generation platform and based on the analysis of the first data and the second data, a mitigation output indicating a level of inconsistency between the first data and the second data, the level of inconsistency indicating a probability of fraud during the onboarding process;

determining based on the mitigation output, eligibility for the requested product; and generating and sending an instruction to the computing device to cause the computing device to output an indication of the eligibility, wherein the first and second data are personal health data of a user of the computing device.

10. The one or more tangible non-transitory computer-readable storage media of claim 9, wherein the personal health data includes one or more of fitness/activity data, location data, purchase history data, credit history data, motor vehicle records (MVRs) data, medical information bureau (MIB) data, medical billing records data, medical prescription data, and social networking data.

11. The one or more tangible non-transitory computer-readable storage media of claim 9, wherein the database is a prescription database, and
wherein analyzing the first data and the second data for inconsistencies includes:
determining, from the first data, information related to one or more first prescriptions stored in the personal health data;
determining, from the second data, information related to one or more second prescriptions stored in the prescription database;
comparing the information related to the one or more first prescriptions to the information related to the one or more second prescriptions;
determining, based on the comparison, a number of differences between the information related to the one or more first prescriptions and the information related to the one or more second prescriptions; and
identifying an inconsistency, based on determining that the number of differences between the information related to the one or more first prescriptions and the information related to the one or more second prescriptions exceeds a predetermined threshold.

12. The one or more tangible non-transitory computer-readable storage media of claim 9, wherein the first data source comprises a prescription database, and
wherein analyzing the first data and the second data for inconsistencies includes:
determining, from the first data, information related to a prescription of the user of the computing device;
determining, from the second data, information related to a medical condition of the user;
determining whether the information related to the prescription of the user is compatible with the information related to the medical condition of the user; and
identifying an inconsistency, based on determining that the information related to the prescription of the user is incompatible with the information related to the medical condition of the user.

13. The one or more tangible non-transitory computer-readable storage media of claim 9, wherein the first data source comprises health records, and
wherein analyzing the first data and the second data for inconsistencies comprises:
determining, from the first data, first electrocardiogram (ECG) data associated with the user of the computing device;
determining, from the second data, second ECG data associated with the user of the computing device; and
identifying an inconsistency, based on determining that a pattern of the first ECG data and a pattern of the second ECG data differ by greater than a predetermined threshold.

14. The one or more tangible non-transitory computer-readable storage media of claim 13, where the sensor associated with the computing device is disposed in a wearable device.

15. The one or more tangible non-transitory computer-readable storage media of claim 9, wherein the mitigation output includes a fraud probability confidence score determined based on the analysis of the first data and the second data.

16. A method comprising:
receiving, from a computing device, a request to purchase a product at an onboarding and policy management platform, the computing device in communication with the onboarding and policy management platform over a network;
sending, to the computing device and based on the request to purchase the product, instructions to collect data from the computing device;
receiving, from a sensor of the computing device, first data of a first type;
receiving, from a sensor device, second data of a second type different from the first type, wherein the first and second data are personal health data of a user of the computing device;
analyzing the first data and the second data for inconsistencies using a mitigation analysis and output generation platform;
determining, using the mitigation analysis and output generation platform and based on the analysis of the first data and the second data, a mitigation output indicating a level of inconsistency between the first data and the second data, the level of inconsistency indicating a probability of fraud;
determining, based on the mitigation output, eligibility for the requested product; and
generating and sending an indication of the eligibility to one or more of the computing device and the sensor device to cause one or more of the computing device and the sensor device to output the indication.

17. The method of claim 16, wherein the personal health data includes one or more of fitness/activity data, location data, purchase history data, credit history data, motor vehicle records (MVRs) data, medical information bureau (MIB) data, medical billing records data, medical prescription data, and social networking data.

18. The method of claim 16, wherein the first data comprises a count of steps taken by the user of the computing device during a first period of time and the second data comprises a heart rate of the user during the first period of time, and wherein analyzing the first data and the second data for inconsistencies comprises:
  determining, from the first data, a first identifier identifying the computing device used to collect the first data;
  determining, from the second data, a second identifier identifying the sensor device used to collect the second data;
  comparing the first identifier and the second identifier; and
  identifying an inconsistency, based on determining that the first identifier and the second identifier differ.

19. The method of claim 16, wherein the first data comprises a count of steps taken by the user of the computing device during a first time period and the second data comprises a sleep pattern of the user during the first time period, and
  wherein analyzing the first data and the second data for inconsistencies comprises:
    determining, from the first data, whether the count of steps during the first time period exceeds a predetermined threshold;
    determining, from the second data, whether the sleep pattern indicates that the user was sleeping during the first time period; and
    identifying an inconsistency, based on determining that the count of steps during the first time period exceeds the predetermined threshold and determining that the sleep pattern indicates that the user was sleeping during the first time period.

20. The method of claim 16, wherein the first data comprises a count of steps taken by the user of the computing device during a first period of time and the second data comprises movement data during the first period of time, and
  wherein analyzing the first data and the second data for inconsistencies comprises:
    determining, from the first data, whether the count of steps was entered manually;
    determining, from the second data, whether the movement data indicates movement at a speed greater than a predetermined threshold; and
    identifying an inconsistency, based on determining that the count of steps was entered manually and the movement data indicates movement at a speed greater than the predetermined threshold.

* * * * *